United States Patent [19]

Hall et al.

[11] 4,170,576

[45] Oct. 9, 1979

[54] USES OF MIXTURES OF ALPHA METHYL STYRENE DIMERS AND TERPENE DIMERS IN PERFUMERY PROCESSES AND PRODUCTS

[75] Inventors: John B. Hall, Rumson; Wilhelmus J. Wiegers, Red Bank; Ira D. Hill, Locust; Robert M. Novak, Fords; Frederick L. Schmitt, Holmdel, all of N.J.

[73] Assignee: International Flavors & Fragrances Inc., New York, N.Y.

[21] Appl. No.: 923,183

[22] Filed: Jul. 10, 1978

[51] Int. Cl.² .................................................. C11B 9/00
[52] U.S. Cl. ..................................... 252/522; 585/20; 585/22; 585/23; 585/25; 585/27
[58] Field of Search ............................................ 252/522

[56] References Cited

U.S. PATENT DOCUMENTS

| | | | |
|---|---|---|---|
| 2,249,112 | 7/1941 | Carmody | 260/666 R |
| 2,422,145 | 6/1947 | Taylor | 252/522 |
| 3,415,893 | 12/1968 | Sellers et al. | 568/820 |
| 3,502,769 | 3/1970 | Fukuhara | 252/522 |
| 3,673,120 | 6/1972 | Janes et al. | 252/522 |

FOREIGN PATENT DOCUMENTS 7392355 11/1973 Japan.

OTHER PUBLICATIONS

Chem. Ab. 45:5880h, 1951.

*Primary Examiner*—Veronica O'Keefe
*Attorney, Agent, or Firm*—Arthur L. Liberman; Franklin D. Wolffe

[57] ABSTRACT

A process is described for providing clear extended compositions of essential oils which comprises a composition of an essential oil and an extender material miscible with said essential oil which does not appreciably alter the aroma of the essential oil insofar as its quality or strength is concerned, the proportion of essential oil in extender material being from about 70% up to about 99%, said extender material being a mixture of (A) a dimerization product of an alpha methyl styrene or a methyl or other $C_2$–$C_4$ lower alkyl homologue thereof or mixture of same, and (B) one or more "dimerization" (or "coupling") products of one or more terpenes which are monocyclic and have two carbon-carbon double bonds or which are bicyclic and have one carbon-carbon double bond or one or more hydrogenated derivatives thereof or mixtures of same.

23 Claims, 15 Drawing Figures

FIG.I

GLC PROFILE FOR EXAMPLE I, FRACTION 19.

FIG. 2 IR SPECTRUM FOR EXAMPLE I, FRACTION 19

GLC PROFILE FOR EXAMPLE I, FRACTION 3.

NMR SPECTRUM FOR EXAMPLE I, FRACTION 3 AND EXAMPLE III

SOLVENT: CDCl₃
SWEEP WIDTH: 1500 Hz.

MASS SPECTRUM FOR EXAMPLE I, FRACTION 3, AND EXAMPLE III.

GLC PROFILE FOR EXAMPLE III, FRACTIONS 9-12.

GLC PROFILE FOR EXAMPLE IV(B)

NMR SPECTRUM FOR EXAMPLE IV(A)

I R SPECTRUM FOR EXAMPLE IV(A)

GLC PROFILE FOR EXAMPLE IV(C)

NMR SPECTRUM FOR EXAMPLE IV(C)

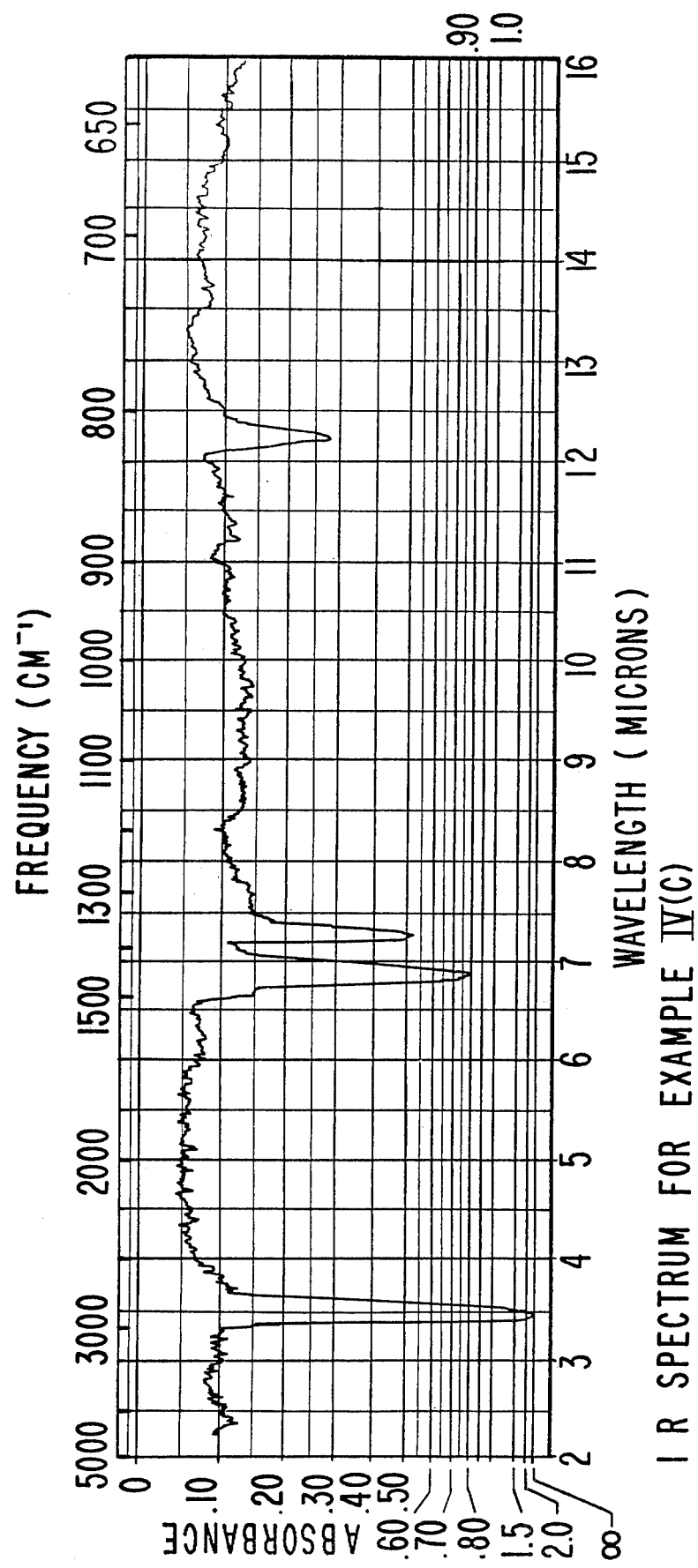

USES OF MIXTURES OF ALPHA METHYL STYRENE DIMERS AND TERPENE DIMERS IN PERFUMERY PROCESSES AND PRODUCTS

BACKGROUND OF THE INVENTION

Compounded perfumery compositions contain a number of ingredients which may be of natural or synthetic origin. The ingredients are blended by the perfumer to create the desired odor effect. Such essential oils which contain high percentages of hydrocarbon constituents such as patchouli oil (an essential oil derived from Pogostemon Patchouli) have, for example, warm aromatic spicy odors. When the perfumer wishes to include this type of note for example in a perfumery composition of an oriental type, he will use patchouli oil. However, such natural oils as oil of patchouli are expensive essential oils and are of limited availability. Even more extreme examples are natural sandalwood oil and natural vetiver oil. Although, attempts have been made to simulate the odor of patchouli oil, sandalwood oil, and vetiver oil by use of blends of synthetic perfumery chemicals, the creation of such oils having identical aromas with reference to the natural oils has not been achieved.

In U.S. Pat. No. 3,673,120 issued on June 27, 1972, 8-camphene carbinol was indicated to be useful as a perfumery extender for patchouli oil in perfumery compositions when present in a concentration of from 1 to 200 parts by weight per 100 parts by weight of the patchouli oil. However, 8-camphene carbinol has the disadvantage of significantly decreasing the aroma strength of the patchouli oil and is not versatile for use with oils other than patchouli oil, for example, vetiver oil and sandalwood oil in the genus of natural oils, and synthetic oils, for example, geranonitrile and cinnamonitrile.

In U.S. Pat. No. 2,422,145 issued on June 10, 1947, water-soluble hydroxy polyoxyethylene ethers of partial higher fatty acid esters of low molecular weight polyhydroxylic compounds were found to form clear extended solutions with essential oils which could be used as such or which could be diluted with water to form stable dispersions or solutions of essential oils. Specifically disclosed are compositions containing clear, stable solutions of a quantity of an essential oil and at least an equal quantity of such ethers as mannitan monopalmitate hydroxy polyoxyethylene ether with about 20 oxyethylene units per mole with such solution being capable, upon dilution with water, of forming a clear, stable aqueous dispersion of essential oil and hydroxy polyoxyethylene ether. U.S. Pat. No. 2,422,145, however, does not disclose the formation of solutions of essential oil in organic solvents which are immiscible with water. Furthermore, the ethers of U.S. Pat. No. 2,422,145 significantly reduce the strength of the perfumery material when used in conjunction with same.

Cyclohexane dicarboxylic acid diesters having the structure:

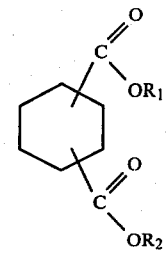

where $R_1$ and $R_2$ are less than 13 carbon aliphatic or alicyclic hydrocarbon moieties are disclosed to be useful "perfume harmonizing agents" in Japanese Published Application at J 52136927 issued on Nov. 15, 1977 to Asahi Denka Kogyo. However, such materials as these cyclohexane dicarboxylic acid diesters detract from the strength of the perfume material with which it is used.

Processes for preparing alpha methyl styrene dimers and methyl homologues thereof are broadly disclosed in the prior art, for example:

French Pat. No. 1,317,412 assigned to Socony Mobil Oil Company dated Feb. 8, 1963;

U.S. Pat. No. 3,161,692 issued on Dec. 15, 1964 assigned to Socony Mobil Oil Company;

U.S.S.R. Pat. No. 191,511 issued on Jan. 26, 1967;

U.S. Pat. No. 3,523,981 assigned to Olin Corporation, issued on Aug. 11, 1970;

Deutsche Offenlegungsschrift 2,101,089 issued on Aug. 10, 1972;

U.S. Pat. No. 3,890,402 assigned to Phillips Petroleum Company, issued on June 17, 1975;

Petropoulos and Fisher, J.Am.Chem.Soc. 80, 1938-41 (1958); and

U.S. Pat. No. 4,081,489 issued on Mar. 28, 1978

U.S. Pat. No. 4,081,489 discloses an improved process for the production of compounds having the formula

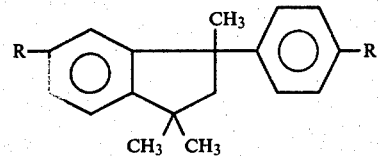

wherein R is independently hydrogen or methyl by contacting a compound of Formula I:

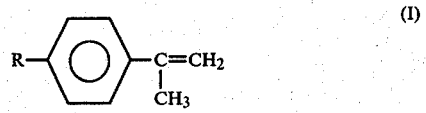

where mixture of compounds of Formula I, wherein R is hydrogen or methyl, with a sulfuric acid catalyst at a temperature of 100° to 225° C. which comprises employing a catalyst consisting essentially of about 0.05 up to about 3 weight percent based on the weight of the compound or mixture of compounds of Formula I, of 90 to 98% concentrated sulfuric acid.

Nothing in the prior art teaches the use of alpha methyl styrene dimers, methyl homologues thereof or hydrogenated derivatives thereof as perfume diluents or as perfume extenders. Furthermore, nothing in the prior art teaches the use of hydrogenated derivatives of such alpha methyl styrene dimers or methyl homologues thereof.

In U.S. Pat. No. 3,415,893 issued on Dec. 10, 1968, synthetic pine oil, a material well known to be useful in the perfumery arts was indicated to be synthesized in such a manner that alpha pinene and aqueous sulfuric acid containing emulsifier were agitated under controlled temperature conditions until the content of terpene alcohols reached a maximum. The oil and aqueous phases, in U.S. Pat. No. 3,415,893, are then separated and the oil phase is washed with water containing basic materials to neutralize any residual acid. The oil phase is then distilled to separate the pine oil product from "unreacted alpha pinene and other terpenes, if present as well as from the by-products of the reaction". It is indicated that the by-products are primarily monocyclic hydrocarbons containing some cineols, cyclic ethers and other undesirable products of the reaction and that the by-product portion is a useful solvent. Nothing in U.S. Pat. No. 3,145,893 discloses the usefulness of the diterpene—alpha methyl styrene dimer mixtures of our invention and the advantages thereof as extenders in perfumery.

Diterpenes and hydrogenated diterpenes resulting from the action of various acids on monoterpenes have been studied by various investigators since the discovery over a century ago of dipinene by Deville, Ann. Chim. Phys. [2] 75, 66 (1840) and Ann. Chim. 37, 192 (1840) who obtained dipinene from terpentine oil and sulfuric acid. These experiments of Deville were reviewed as was the literature of synthetic dipinenes in general, by Dulou, Chimie et Industrie, 27 (Special Number) 651 (1932) wherein compounds having the structures of dipinene, indicated to be:

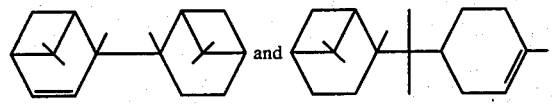

were stated to be produced from alpha pinene having the structure:

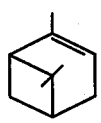

Di-alpha pinene was also produced by Kuwata, J. Faculty Eng. Tokyo Imp. Univ. 18 117–24 (1929) by the action of Japanese acid clay on d-alpha-pinene. In a two-stage reaction, Venable, J. Am. Chem. Soc. 45, 728-34 (1923) treated alpha pinene with Fullers earth causing it first to undergo a molecular rearrangement and then causing a subsequent polymerization to dipinene. Kuwata, in J. Soc. Chem. Ind. Japan 36, Suppl. binding 256-8 (1933) [abstracted in Chem. Abstracts 27:3927] discloses the treatment of camphene in a benzene solution with Japanese acid clay yielding dimer. Camphene dimers are also disclosed to be produced in Japanese Kokai 73 92,355 of Nov. 30, 1973 wherein camphene is passed through a strongly acidic cation exchange resin at one atmosphere and in vacuo at less than or equal to 130° C. to produce camphene dimers and trimers. Japanese Kokai 73 92,355 (Patent Application No. 27686/72) contains the following claim:

"The process to manufacture oligomers of camphene by the polymerization of camphene at less than 130° C. and under atmospheric or reduced pressure with the catalysts of ion exchange resin of strong acid type."

In addition, Japanese Kokai 73 92,355 also contains the following relevant disclosure:

"By this invention, the produced oligomers are removed from the reaction system, therefore eliminating the chances of side reactions such as isomerization, hydrolysis, dehydration and oxidation. The products can be obtained in high yield without tetramer or higher oligomers, and are colorless and odorless which are suitable for use in fragrances, cosmetics and food additives."

The specific properties of the camphene dimers and their utility in the manner described herein as perfumery extenders and diluents are not disclosed in Japanese Kokai 73 92,355, however.

The dimer of limonene is indicated to be prepared from d-limonene by Beilstein V. 509, page 246 (No. 9). The presence of the dimer of limonene is indicated to exist in the essence of Dictamnus Hispanicus in Chem. Abstracts 45:5880 [abstract of "The Essence of Dictamnus Hispanicus", J. Sistare (Inst. 'Alonso Barba' Barcelona, Spain) Anales Real Soc. Espan. Fis. Ey. Quim. 47 B, 171-4 (1951)].

In U.S. Pat. No. 2,249,112 issued on July 15, 1941, hydrogenated pinene polymers are indicated to be useful for their "solubility-viscosity characteristics", making them usable as impregnants, adhesive materials, and as a vehicle for metallic paints. They are also indicated to be competable with many mineral oils and can be blended with rubber to produce soft tacky compositions. The hydrogenated pinene polymers indicated to be so produced in U.S. Pat. No. 2,249,112 are produced according to the following reaction scheme:

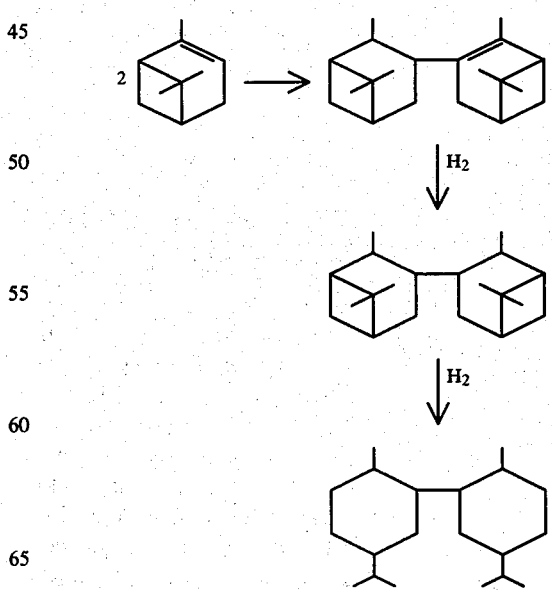

and stated to have the structures:

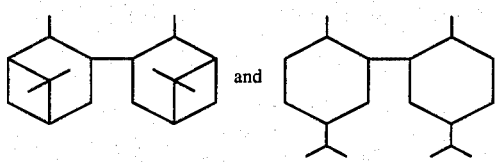

The hydrogenated terpene polymers of 2,249,112 are not taught to be useful as perfume extenders and are not indicated to have the properties in conjunction with certain perfume essential oils as is disclosed and claimed in the instant application.

Perfume extenders have been broadly used as "adulterants" in the art of perfumery. Thus, for example, in the text entitled "The Art of Perfumery and Method for Obtaining the Odors of Plants" authored by Piesse (Lindsay and Blakiston, Publishers, Philadelphia, 1856) turpentine and spike oil are indicated to be adulterants for lavender oil on page 255. In Poucher "Perfumes and Cosmetics" Van Nostrand Company 1923 terpene residues obtained during the manufacture of concentrated lemon oil are indicated to be adulterants for lemon oil. In Vol. 1 of "The Essential Oils", Guenther, Krieger Publishing Company 1975, Vol. 1 Terpinyl Acetate, and Turpentine Oil (containing d-alpha pinene) are indicated to be used as adulterants. In Vol. 2 of "The Essential Oils" camphorene, a "diterpene" is indicated to be widely applied as fixatives in the sending of soaps. Alpha camphorene has the structure:

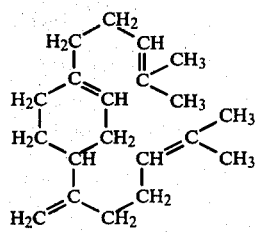

U.S. Pat. No. 3,502,769 issued on Mar. 24, 1970, (Fukuhara) discloses a toilet preparation containing a storage-stabilizing amount of a hydrocarbon which may be a mono-cyclic hydrogenated terpene polymer of the formula $(C_{10}H_{19})_n$ and/or a bi-cyclic hydrogenated terpene polymer of the formula $(C_{10}H_{17})_n$ where n is a whole number of from 2 to 4 and a cosmetic base, such as a cold cream or a cleansing cream base. In column 2 of U.S. Pat. No. 3,502,769 at line 15, it is indicated that the hydrogenated terpenes are produced from alicyclic terpene hydrocarbons. It is further indicated that, for example, mono-cyclic terpenes such as menthadienes (e.g., α-terpinene, γ-terpinene, α-phellandrene, β-phellandrene, terpinolene, limonene, etc.) and bi-cyclic terpenes such as the camphenes are first polymerized to form hydrocarbon compounds of the formula $(C_{10}H_{16})_n$, wherein n is a positive whole number from 2 to 4. It is further specified that these polymers are either dimers, trimers or tetramers, and that the resultant polymers are then completely hydrogenated and in the case of the menthadienes, form mono-cyclic polymers of the formula $(C_{10}H_{19})_n$, wherein n is a whole number of from 2 to 4, and in the case of the bi-cyclic terpenes, it is indicated that there are formed bi-cyclic polymers of the formula $(C_{10}H_{17})_n$ wherein n is a whole number of from 2 ro 4. As an example, when using dipentene as the starting material, the following reaction sequence is stated to take place:

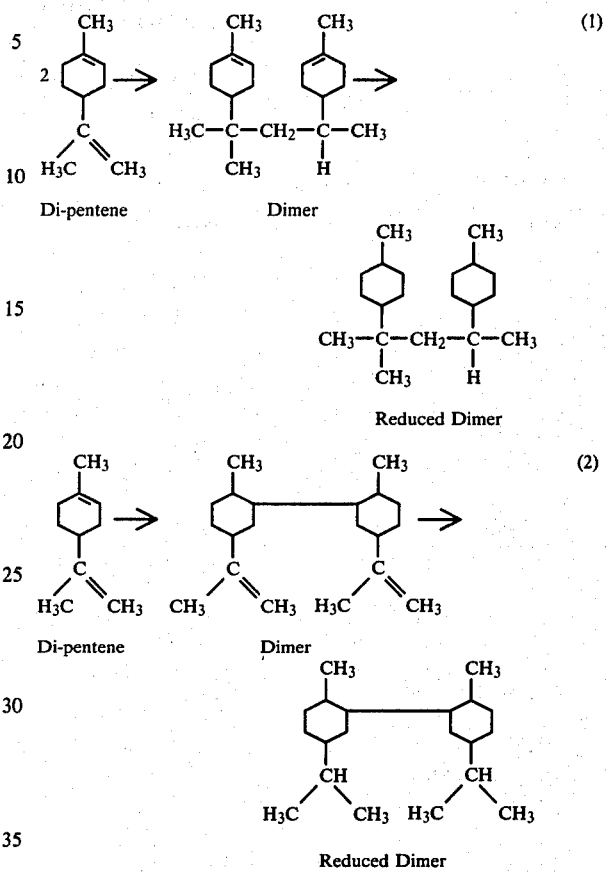

Although perfumes are shown to be usable in conjunction with the hydrogenated terpene polymer materials which are further used for the purpose of storage-stabilization, there is no teaching in U.S. Pat. No. 3,502,769 that, in the proportions indicated, the mixtures of (i) such terpene dimerization products as dimerization products of camphene or of α-pinene or β-pinene and (ii) α-methyl styrene dimerization products of our invention are useful in the manner described herein as perfumery extenders and diluents.

Plyusnin, et al. in the U.S.S.R. Journal of Applied Chemistry, 29, 1363–1367 also discloses polymerization of individual terpenes (α-pinene, dipentene and camphene) in the presence of hydrogen fluoride but does not set forth the use of the mixture of our invention in the manner described herein as perfumery extenders and diluents.

Thus, there is no suggestion in the prior art that the mixtures of (i) such terpene dimerization products as dimerization products of camphene or of α-pinene or β-pinene and (ii) α-methyl styrene dimers of our invention are useful in the manner described herein as perfumery extenders and diluents.

BRIEF DESCRIPTION OF THE DRAWINGS

FIG. 15 is the infrared spectrum for the product produced according to Example IV (C), the dimer of limonene.

THE INVENTION

Figure 1:
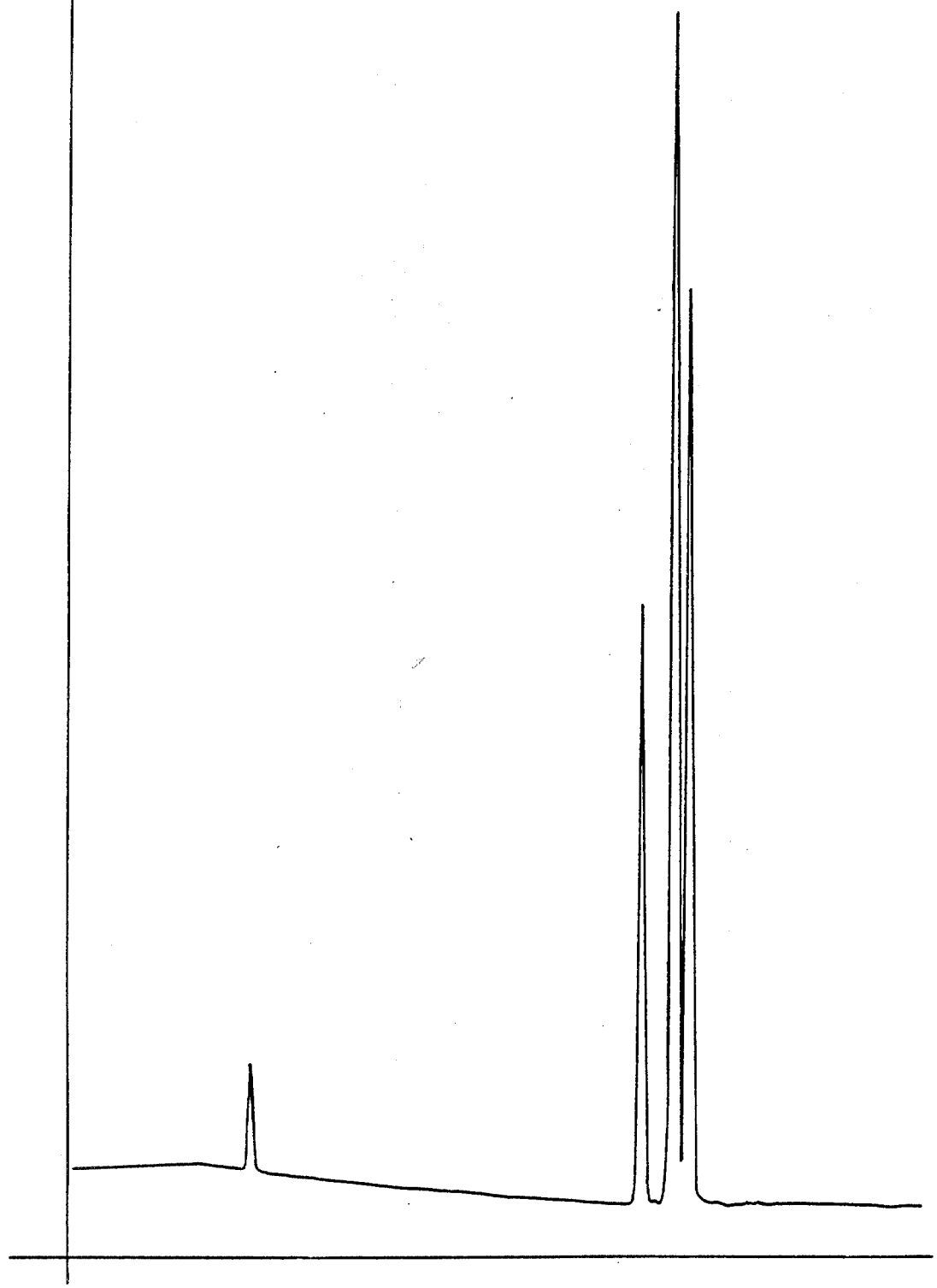
FIG. 1 is the GLC profile for the product produced according to Example I, Fraction 19.

Surprisingly, it has been found that mixtures of (A) dimerization products of (i) monocyclic terpenes containing two carbon-carbon double bonds, (ii) bicyclic terpenes containing one carbon-carbon double bond and (iii) a monocyclic terpene containing two carbon-carbon double bonds and a bicyclic terpene containing one carbon-carbon double bond or mixtures of same or hydrogenation products thereof or mixtures of said hydrogenation products and said dimerization products and (B) alpha methyl styrene dimerization products, dimerization products of methyl or other $C_2$–$C_4$ lower alkyl homologues thereof and hydrogenated derivatives thereof may be used as diluents or extenders of various perfumery materials without appreciable loss of the characteristic odor effect of such perfumery materials.

Dimerization products (A) are produced by dimerizing such compounds as camphene having the structure:

or alpha pinene having the structure:

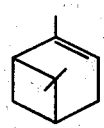

or d-limonene having the structure:

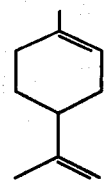

or alpha phellandrene having the structure:

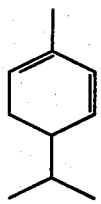

or gamma-terpinene having the structure:

or delta$^3$-carene having the structure:

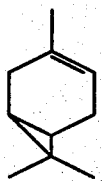

or beta phellandrene having the structure:

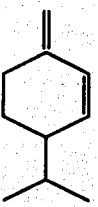

or beta-terpinene having the structure:

or alpha terpinene having the structure:

or terpinolene having the structure:

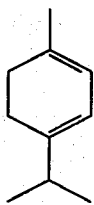

or beta pinene having the structure:

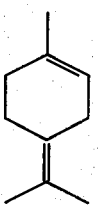

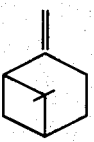

or by "dimerizing" mixtures of two or more of such compounds, such as the mixture of $C_{10}$ terpenes commonly known as "sulfate turpentine" or by "dimerizing" a $C_{10}$ terpene and a dehydrogenated terpene (e.g., cymene) in the presence of acid catalysts, such as sulfuric acid and hydrofluoric acid or in the presence of acid clay catalysts, such as Japanese Acid Clay or Fullers earth or cation exchange resin catalysts. The said "dimerization" products are compounds having such possible structures as:

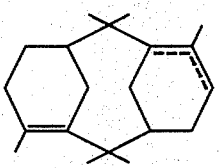

and the hydrogenation products thereof have such possible structures as:

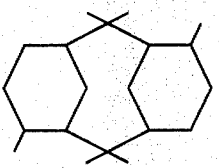

Insofar as the dimerization products (A) are concerned, the terms "dimerization product" and "dimer" are intended to cover reaction products containing 20 carbon atoms resulting from the reaction of a 10 carbon atom terpene compound (monocyclic with two double bonds or bicyclic with one carbon-carbon double bond) with itself or with another terpene compound which is monocyclic or bicyclic, without regard to the number of hydrogen atoms contained in any molecules of said reaction products.

Dimerization products (B) produced by dimerizing alpha methyl styrene having the structure:

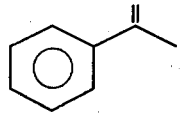

or by dimerizing a methyl or other $C_2$–$C_4$ lower alkyl homologue thereof having, for example, the structure:

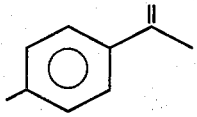

in the presence of Lewis Acid catalysts, Bronstedt acid catalysts such as sulfuric acid or in the presence of acid clay catalysts such as Japanese Acid Clay or Fullers earth or cation exchange resin ctalysts. The dimerization product of alpha methyl styrene so useful have the structures:

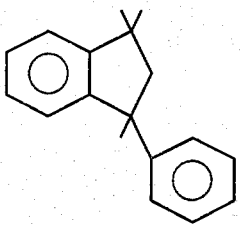

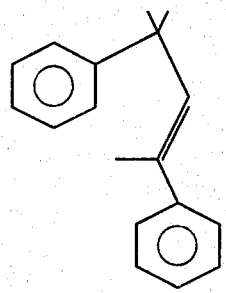

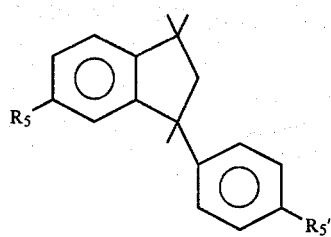

and

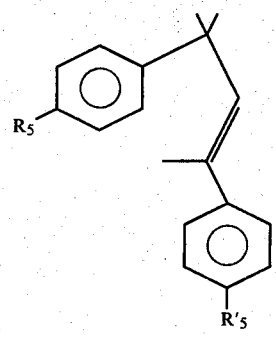
wherein one of $R_5$ or $R_5'$ is methyl or other $C_2$–$C_4$ lower alkyl and the other of $R_5$ or $R_5'$ is hydrogen or each of $R_5$ and $R_5'$ are the same or different $C_1$–$C_4$ lower alkyl, e.g., methyl. Hydrogenation products thereof have the structures:
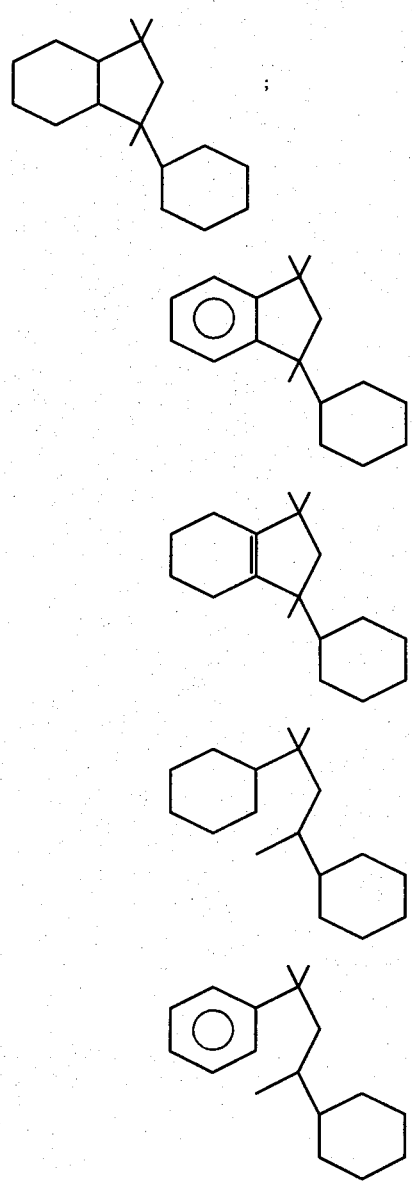
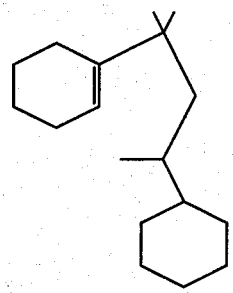
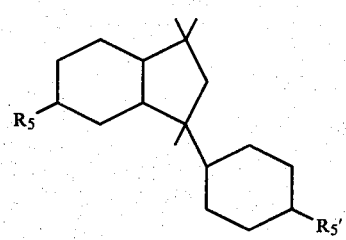
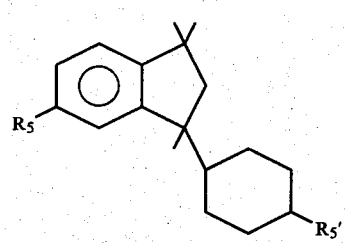
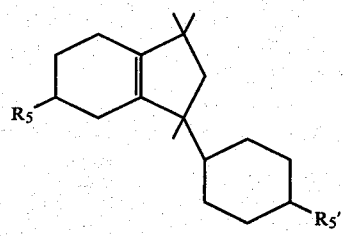
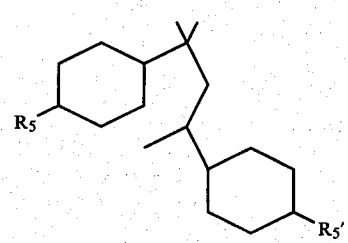
and
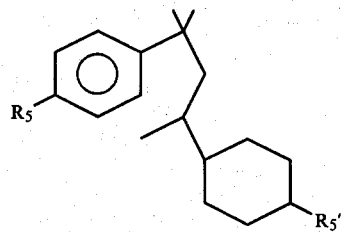

-continued

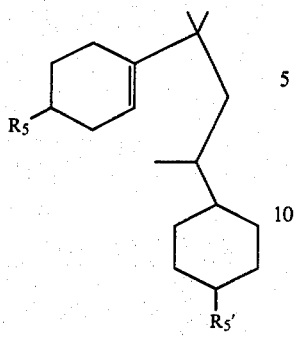

wherein one or both of $R_5$ and $R_5'$ is methyl or other $C_2$–$C_4$ lower alkyl. Such hydrogenation products can be represented by the generic structures:

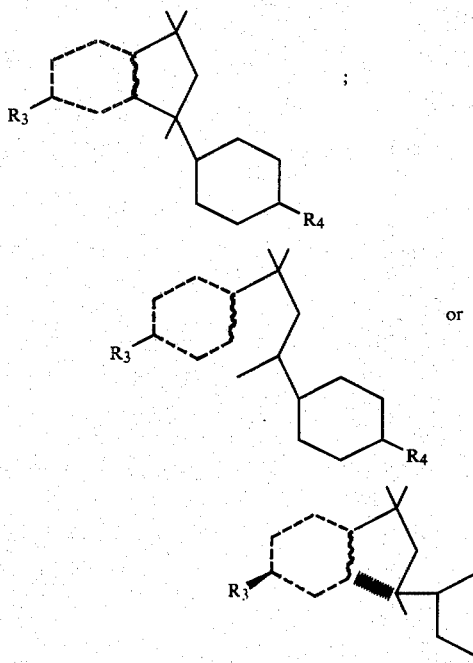

wherein $R_3$ and $R_4$ are the same or different and represent hydrogen or methyl or other $C_2$–$C_4$ lower alkyl; wherein the dashed lines and wavy line represent carbon-carbon single bonds or carbon-carbon double bonds with the proviso that when there is one double bond present, only the wavy line is a double bond and when there is more than one double bond present, the ring containing the dashed lines and the wavy line is a benzene ring and where the line ∥∥ represents either a carbon-carbon single bond or no bond.

In the case of the hydrogenation product, when $R_3$ and/or $R_4$ are lower alkyl, for example, methyl, the methyl groups may be in a "cis" or "trans" relationship to one another and with respect to the cyclohexyl moieties.

A significant property of the above-said mixtures of dimerization products and hydrogenated dimerization products is that they have a broad range of solubilities for various types of perfumery materials including complete solubility for certain alcohols, esters, pyrans, aldehydes, ketones, cyclic ethers, cyclic amines, nitriles and natural oils. Thus, for example, the following materials are completely miscible with the dimers which are the subject of our invention.

Phenyl Ethyl Alcohol
Geraniol
Terpineol
Citronellyl Acetate
Decyl Acetate
Rose Oxide
n-Decanal
Citral
Alpha Ionone
Eugenol
Galaxolide
2-Methyl-2-Pentenoic Acid
Isobutyl Quinoline
Lemon Oil
Rosemary Oil
Patchouli Oil
Cinnamonitrile
Geranonitrile This, it has been discovered that the dimers of our invention can be used as partial replacements for certain essential oils and synthetic substitutes therefor in compounded single phase liquid perfumery compositions.

Accordingly, the present invention comprises a compounded single phase liquid perfumery composition which comprises one or more synthetic perfume oils or natural perfume oils or mixtures of natural perfume oils and synthetic perfume oils with which there has been incorporated from about 1 up to about 30 parts of a mixture of (A) an alpha methyl styrene or alpha methyl styrene methyl or other $C_2$–$C_4$ lower alkyl homologue dimerization product of hydrogenated derivative thereof or mixture of alpha methyl styrene or alpha methyl styrene methyl (or other $C_2$–$C_4$ lower alkyl) homologue dimerization product and one or more hydrogenated derivatives thereof which have at least one of the following structures:

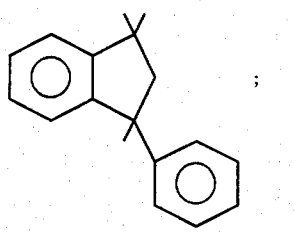

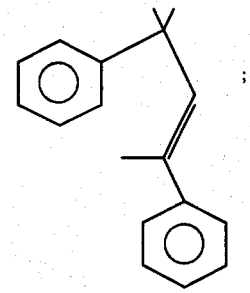

-continued
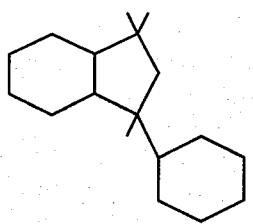;
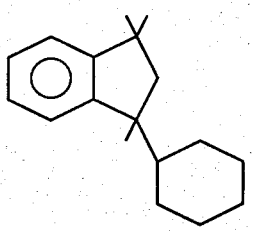;
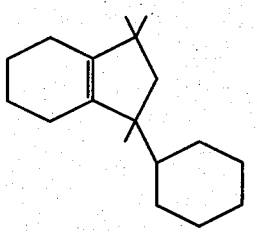;
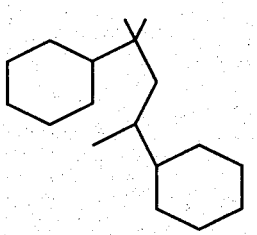;
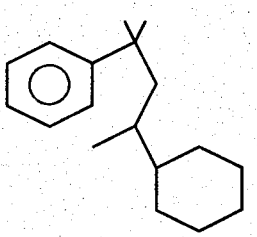;
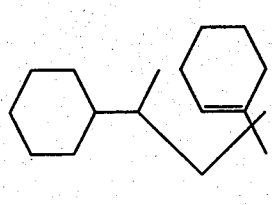;
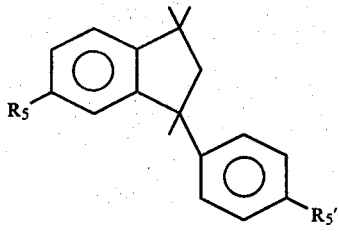;
-continued
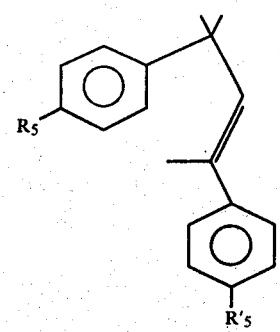
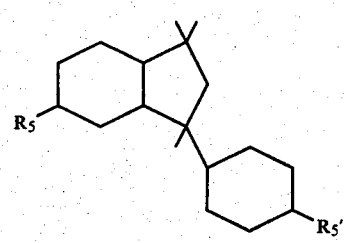;
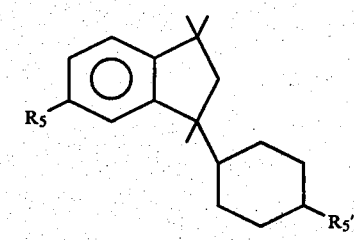
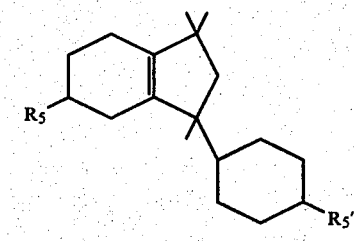
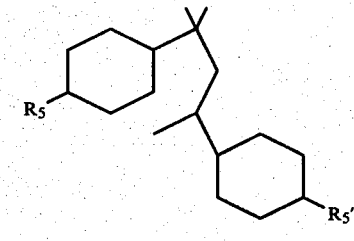
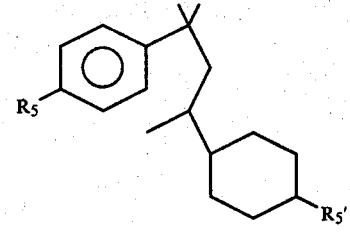 and/or

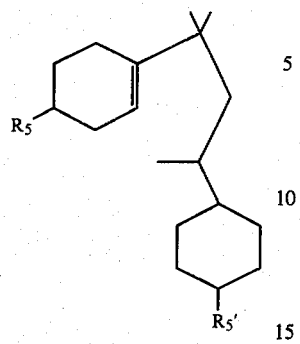

wherein one or both of $R_5$ and $R_5'$ is methyl or other $C_2$–$C_4$ lower alkyl. (These compounds being represented collectively by the generic structures:

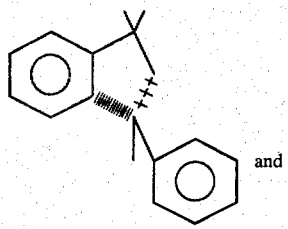 and

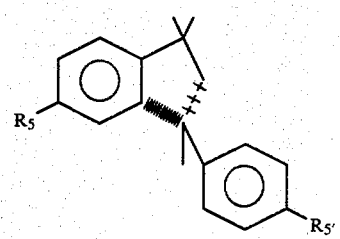

in the case of alpha methyl styrene dimerization products and dimerization products of methyl or other $C_2$–$C_4$ lower alkyl homologues thereof and the structures:

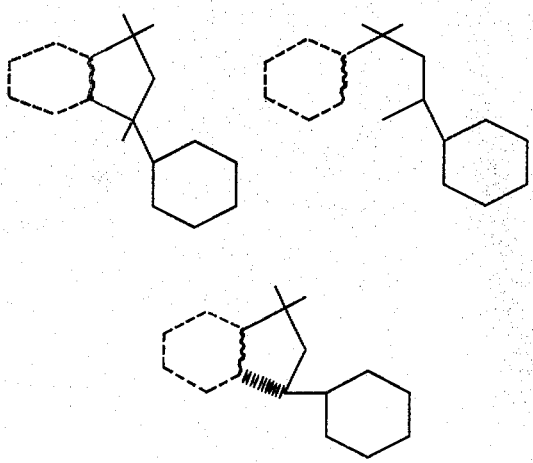

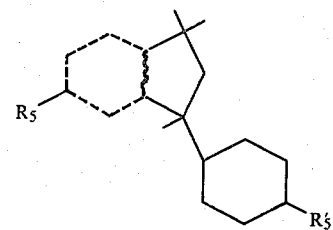

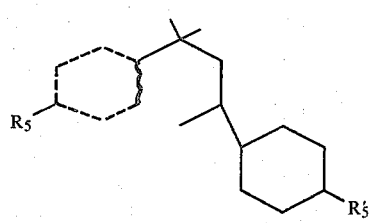

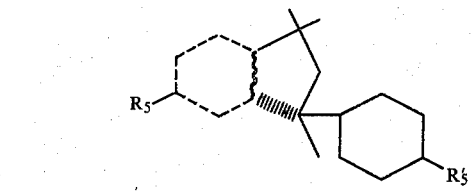

wherein one of $R_5$ and $R_5'$ is methyl or other $C_2$–$C_4$ lower alkyl and the other is hydrogen, or both $R_5$ and $R_5'$ are methyl or other $C_2$–$C_4$ lower alkyl in the case of the hydrogenated derivatives thereof wherein the dashed lines and wavy lines represent carbon-carbon single bonds or carbon-carbon double bonds with the proviso that when there is one double bond present in the ring containing the dashed lines and wavy lines, only the wavy line is a double bond and when there is more than one double bond present, the ring containing the dashed lines and the wavy lines is a benzene ring; and wherein the line | | | | represents either a carbon-carbon single bond or no bond; and wherein the line + + + + + represents a carbon-carbon single bond or a carbon-carbon double bond with the proviso that when the line + + + + is a carbon-carbon double bond, the line | | | | is no bond and when the line + + + + is a carbon-carbon single bond, the line | | | | is a carbon-carbon single bond) and (B) a "dimerization" product of (i) a monocyclic terpene containing two carbon-carbon double bonds or (ii) a bicyclic terpene containing one carbon-carbon double bond or (iii) a reaction product of a monocyclic terpene containing two carbon-carbon double bonds and a bicyclic terpene containing one carbon-carbon double bond and/or hydrogenated derivatives thereof per 100 parts of compounded single phase liquid perfumery composition. Specific examples of such dimerization products and hydrogenated derivatives thereof useful in the practice of our invention are:

Dimerization products of alpha pinene;
Dimerization products of beta pinene;
Dimerization products of camphene;
Dimerization products of d-limonene;
Dimerization products of gamma terpinene;
Dimerization products of alpha phellandrene;
Dimerization products of $\Delta^3$-carene;
Dimerization products of beta phellandrene;
Dimerization products of terpinolene;

Mixed dimerization products of alpha phellandrene and Δ³-carene wherein a mixture of the two is subjected to a dimerization reaction;

Mixed dimerization products of alpha phellandrene and gamma terpinene;

Mixed dimerization products of gamma terpinene and beta phellandrene;

Mixed dimerization products of alpha pinene, beta pinene and camphene;

Mixed dimerization products of alpha pinene and Δ³-carene;

Mixed dimerization products of sulfate turpentine;

Mixed dimerization products of terpinolene and gamma terpinene;

Hydrogenated derivatives of any of the foregoing or mixtures thereof

The mixture of the "A" and "B" dimerization products and/or hydrogenated derivatives thereof taken alone or taken together, by themselves, contains no odor and each does not by itself impart any alteration of odor to any of the perfumery materials to which they are added. The above stated dimerization products, hydrogenated derivatives thereof and mixtures thereof may be produced according to any of the known methods in the prior art. Thus, a reaction scheme whereby a dimerization product (B) may be produced useful in our invention and whereby hydrogenated derivatives thereof also useful in our invention are produced and whereby mixtures of such hydrogenated derivatives and dimerization products are produced is exemplified below:

Reaction Scheme #1:

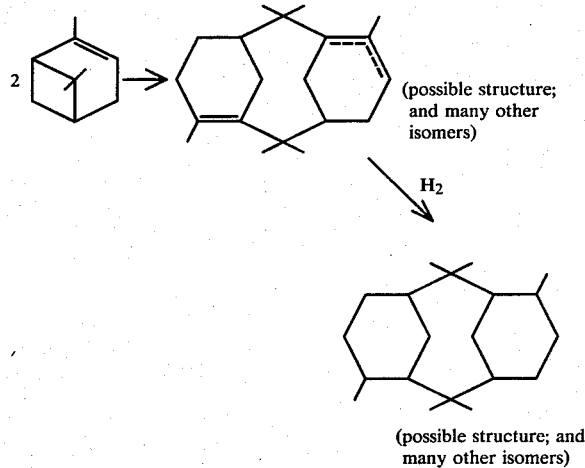

The catalysts useful in producing the dimerization products of ten carbon atom containing terpenes of our invention are Lewis acids such as borontrifluoride, aluminum trichloride, Bronstedt acids such as sulfuric acid and phosphoric acid, ion exchange resin catalysts such as Amberlyst 15, acid clays such as Fullers earth and Japanese Acid Clay. Such dimerization reactions will proceed in the presence of solvents such as cyclohexane, toluene and hexahydro-1,1,2,3,3-pentamethylindane or in the absence of solvents. The temperature of dimerization may vary from 20° C. up to 250° C. A preferred catalyst system with preferred temperature range are borontrifluoride etherate at 0°–100° C. or Acid Clay at 80°–175° C. Atmospheric pressure may be used in the dimerization reaction although higher or lower pressures may also be used without adversely affecting the yield. The weight ratio of ten carbon atom containing terpene monomer:catalyst may vary from 1:0.005 to 1:0.2 with a preferred weight ratio of 1:0.05 up to 1:0.01.

"Turpentines" including "sulfate turpentine", a byproduct of the Kraft (sulfate) pulping process for producing paper are described in a paper by John M. Derfer, entitled "Turpentine as a Source of Perfume and Flavor Materials", *Perfumer and Flavorist International*, Vol. 3, No. 1 at pages 45–50. The composition of the "turpentines" including the above-mentioned "sulfate turpentines" are described therein as follows:

"In all three types of turpentine produced in the southern United States (which is the world's largest producing region), alpha pinene is the most abundant constituent, varying from 60% to 80% (see Table I). Beta pinene is the second most abundant constituent in gum and sulfate turpentine, varying from 25% to 35% in the former, and 20% to 25% in the latter. Wood turpentine contains little, if any, beta pinene. Of the two pinenes, beta pinene is the most versatile chemically. Gum turpentine contains 5% to 8% of monocyclic p-menthadienes, commonly referred to as "dipentene", the trivial name for dl-limonene,

TABLE I

| Component | Composition of Southern Turpentines (%) | | |
|---|---|---|---|
| | Sulfate | Gum | Wood |
| Alpha Pinene | 60–70 | 60–65 | 75–80 |
| Beta Pinene | 20–25 | 25–35 | 0–2 |
| Camphene | Trace | Trace | 4–8 |
| Others | 6–12 | 5–8 | 15–20 | which is the chief component of this p-menthadiene mixture. Sulfate turpentine contains 6% to 12% of this mixture, while wood turpentine contains somewhat more. Sulfate turpentine contains 5% to 10% of oxygenated material from which "natural" pine oil, mostly terpene alcohols, is separated. "Natural" pine oil is also produced in the processing of stumpwood to produce turpentine. Caryophyllene, methylchavicol, and anethole also occur in small amounts in sulfate turpentine.

The composition of turpentine depends not only on the method of isolation, but also on the species and the geographic location of the trees. For example, some western turpentines, as well as certain foreign turpentines, contain appreciable amounts of 3-carene, which finds little other use than as a solvent".

Accordingly, and more specifically, the species of turpentines useful in the practice of our invention, the ten carbon containing terpene ingredients of which are capable of being dimerized to form the dimerization products useful in our invention are as follows:

| Species of Pine from which Turpentine is Derived | Chemical Composition of Turpentine |
|---|---|
| (1) *Pinus albicaulis* Engelmann (Whitebark pine) | Δ³-Carene (35%) Other Terpenes (10%) A Sesquiterpene (7%) A Diterpene (30%) |
| (2) *Pinus Aristata* Engelmann (Bristlecone pine) | dl-and 1-α-Pinene (96%) A Tricyclic Sesquiterpene (4%) |
| (3) *Pinus attenuata* Lemmon (Knobcone pine) | Over 95% d-α-Pinene No β-Pinene or Camphene |

-continued

| Species of Pine from which Turpentine is Derived | Chemical Composition of Turpentine |
|---|---|
| (4) *Pinus balfouriana* Grev. and Balf. (Foxtail pine) | dl-and l-α-Pinene (90%) dl-and l-β-Pinene (2%) dl- and l-Limonene (2%) A Tricyclic Sesquiterpene (4%) |
| (5) *Pinus banksiana* Lambert (Jack pine) | dl- and l-α-Pinene (85%) dl- and l-β-Pinene (10%) |
| (6) *Pinus caribaea* Morelet (Slash pine) | l-α-Pinene (61.5%) l-β-Pinene (34%) Tailings (4.5%) |
| (7) *Pinus clausa* (Engelmann) Vasey (Sand pine) | l-α-Pinene (10%) l-Camphene (10%) l-β-Pinene (75%) |
| (8) *Pinus contorta* var. Latifolia Engelmann (Lodgepole pine) | l-β-Phellandrene |
| (9) *Pinus coulteri* (D. Don (Coulter pine) | n-Heptane (5%) lα-Pinene (30–35%) l-β-Phellandrene (35–45%) n-Undecane (10%) |
| (10) *Pinus echinata* Miller (Shortleaf pine) | d-αPinene (85%) l-β-Pinene (11%) Limonene |
| (11) *Pinus edulis* Engelmann (Pinyon, Colorado pinyon pine) | α-Pinene (70–75%) β-Pinene (5%) α-Cadinene (15–20%) |
| (12) *Pinus flexilis* James (Limber pine) | dl- and l-α-Pinene (80%) Albicaulene-A Monocyclic Sesquiterpene (13%) Bicyclic Sesquiterpene (7%) |
| (13) *Pinus glabra* Walter (Spruce pine) | l-Limonene |
| (14) *Pinus lambertiana* Doulgas (Sugar pine) | l-α-Pinene (65%) l-β-Pinene (13%) Bicyclic Sesquiterpene of Cadalene Type (10%) Lambertol (Sesquiterpene Alcohol $C_{15}H_{26}O$) (2%) |
| (15) *Pinus monophylla* Torrey and Fremont (Single-leaf pinyon) | d-α-Pinene (85%) l-Limonene or Dipentene (4–5%) d-Cadinene (4–6%) |
| (16) *Pinus monticola* Doulgas (Western white pine) | d-α-Pinene (60%) β-Pinene (26%) n-Undecane (1–2%) Sesquiterpenes and perhaps Limonene |
| (17) *Pinus muricata* D. Don (Bishop pine) | d-α-Pinene (98–99%) Camphene (less than 1%) |
| (18) *Pinus palustris* Miller (Longleaf pine) | d-α-Pinene (65%) l-β-Pinene (31.5%) Tailings (3%) |
| (19) *Pinus ponderosa* Lawson (Ponderosa pine) | l-β-Pinene (50%) l-Δ³-Carene (20%) l-Limonene and Dipentene (25%) d-Cadinene (3%) Ponderene (less than 1%) |
| (20) *Pinus ponderosa* var. scopulorum Engelmann (Rocky Mountain ponderosa pine) | d-α-Pinene (60–70%) β-Pinene (5%) Limone (20–25%) |
| (21) *Pinus radiata* D. Don (Monterey pine) | dl-α-Pinene (75%) l-β-Pinene (22%) |
| (22) *Pinus resinosa* Ait. (Red pine) (Norway pine) | α-Pinene |
| (23) *Pinus rigida* var. serotina (Michaux Loudon (Pond pine) | Limonene |
| (24) *Pinus strobus* Linnaeus (Eastern white pine) | dl-α-Pinene (75%) l-β-Pinene (15% Terpene Alcohols and Ketones (4%) |

-continued

| Species of Pine from which Turpentine is Derived | Chemical Composition of Turpentine |
|---|---|
| | A Tricyclic Sesquiterpene (0.3%) |
| (25) *Pinus taeda* Linnaeus (Loblolly pine) | d-α-Pinene (85%) l-β-Pinene (12%) |
| (26) *Pinus torreyana* Parry (Torrey pine) | l-Limonene (75%) n-Decylaldehyde (10%) n-Undecane (5%) Longifolene (4%) Laurylaldehyde (0.2%) Heptane and Nonane (less than 0.1% of each) |
| (27) *Pinus virginiana* Miller (Virginia pine) | dl-α-Pinene (90%) l-α-Pinene (8%) |
| (28) *Pinus washoensis* Mason and Stockwell | d-Δ³-Carene (chiefly), α-Pinene, Dipentene, A Cyclic Sesquiterpene, l-β-Pinene (if Δ³-Carene content is low) |

The dimerization products "A" of our invention and hydrogenated derivatives may be produced according to any of the known methods in the prior art and according to one of the following reaction schemes:

Reaction Scheme #1:

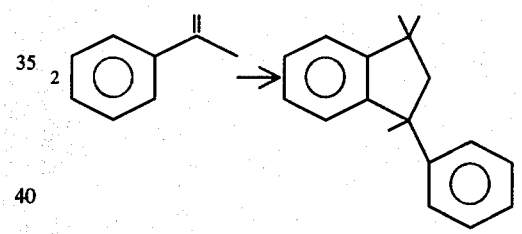

+

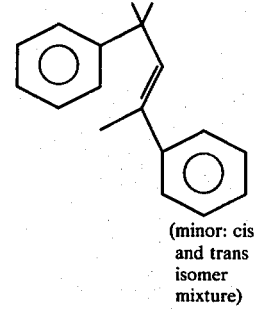

(minor: cis and trans isomer mixture)

Reaction Scheme #2:

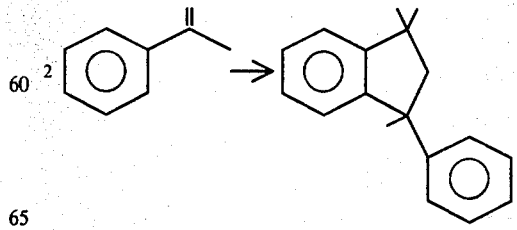

Reaction Scheme #3:

-continued
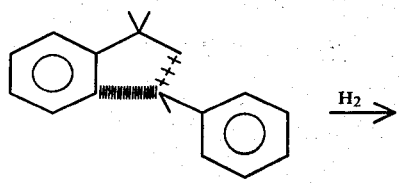
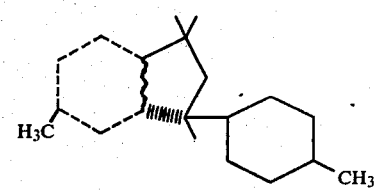
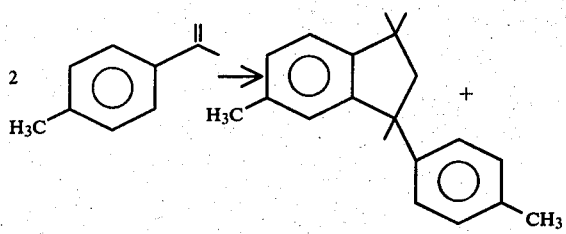
Reaction Scheme #7:
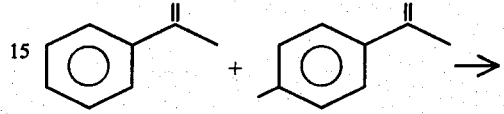
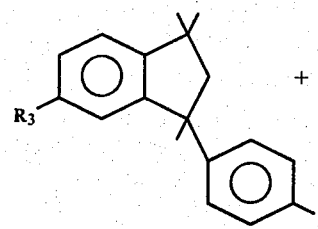
(Mixtures)
Reaction Scheme #4:
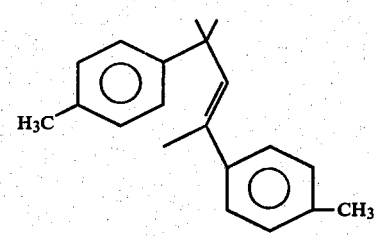
(minor: cis and trans isomer mixture)
(Minor: cis and trans isomer mixtures)
Reaction Scheme #8:
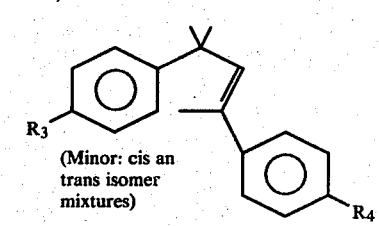
Reaction Scheme #5:
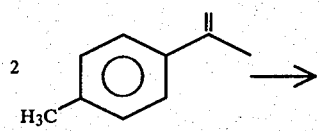
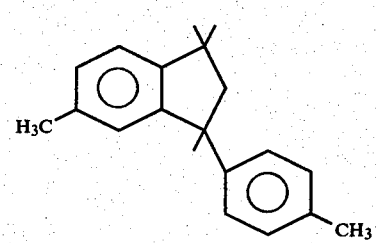
(Mixtures)
Reaction Scheme #6:
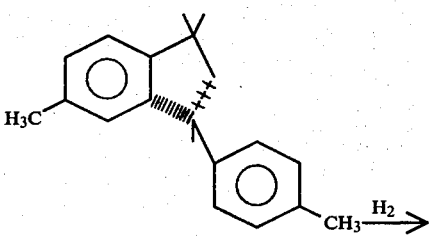
Reaction Scheme #9:
(Mixture)

-continued

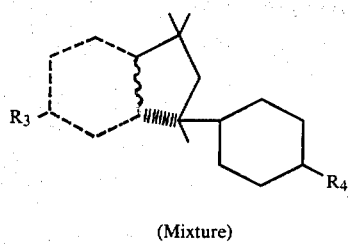

(Mixture)

wherein $R_3$ and $R_4$ are the same or different and represent hydrogen or methyl or other $C_2$–$C_4$ lower alkyl and wherein the dashed lines, the wavy lines, and the line |||| and the line +++ are as defined above.

In this dimerization reaction, the catalysts that may be used are Lewis Acid such as borontriflouride-aluminum trichloride or Bronstedt Acids such as sulfuric acid or phosphoric acid or such acids on carriers such as alumina, silica or cation exchange resin catalysts such as Amberlyst ®15, or acid clay catalysts such as Japanese Acid Clay or Fullers earth. The dimerization reaction is carried out in the presence of a solvent such as cyclohexane, or in the absence of solvent. The temperature range for the dimerization may be from about 20° C. up to about 250° C. with a preferred temperature range when using borontrifluoride etherate of 0°–100° C. or when using acid clays of from 80°–200° C. The pressure at which the reaction may be carried out is conveniently atmospheric pressure but higher pressures or pressures lower than atmospheric may also be used without adversely affecting the yield of product. The weight ratio of alpha methyl styrene or alpha methyl styrene methyl homologue:catalyst is from about 1:0.005 up to about 1:0.2 when using an acid clay catalyst and from about 1:0.1 up to about 1:3 when using, for example, a Bronstedt acid catalyst such as sulfuric acid.

The hydrogenation reaction may be carried out at standard hydrogenation conditions using standard hydrogenation catalysts. Thus, for example, the hydrogenation reaction is carried out in the presence of a palladium on carbon catalyst or a Raney nickle catalyst at temperatures of from about 80° C. up to about 150° C. at pressures of from about four atmospheres up to about thirty atmospheres.

The extended perfumery oils and chemicals of our invention may be used in compositions where the natural oils or chemicals would have been used, for example, in combination with sandalwood oil, vetiver oil, oakmoss, ionone, labdanum, methyl ionone, patchouli oil and other synthetic substitutes therefor.

The extended perfumery materials of our invention will find use as constituents of compounded perfumery compositions in which a number of perfumery materials of natural and/or synthetic origin will be blended together to produce a particular desired odor effect. Such compositions may then be used in space sprays or can be blended in soap, detergent or deodorant compositions, including bath salts, shampoos, toilet waters, face creams, talcum powders, body lotions, sun cream preparations and shave lotions and creams. The perfumery compositions can also be used to perfume substrates such as fibers, fabrics and paper products.

The following examples are given to illustrate embodiments of the invention as it is presently preferred to practice it. It will be understood that these examples are illustrative and the invention is not to be considered as restricted thereto except as indicated in the appended claims.

EXAMPLE I
PREPARATION OF ALPHA METHYL STYRENE DIMERIZATION PRODUCT

Reaction:

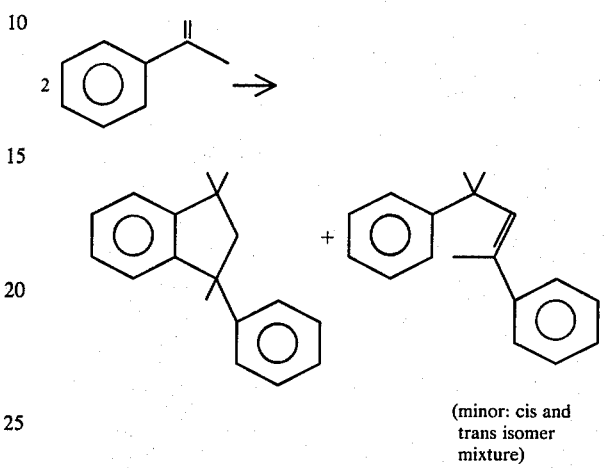

(minor: cis and trans isomer mixture)

Into a two-liter reaction flask equipped with thermometer, reflux condenser, cooling bath, addition funnel, stirrer and gas bubbler is placed 100 g of water. Over a sixteen-minute period, 318 g of concentrated sulfuric acid is added to the water. The contents of the flask is then brought to 30° C. Over a period of two hours after the sulfuric acid is added, while maintaining the temperature of the reaction mass at 20°–33° C., 500 g of alpha methyl styrene is added. After the addition of the alpha methyl styrene, the reaction mass is maintained at a temperature of 30° C. for a period of four hours. 500 g of water is then added following by 250 g of cyclohexane. The reaction mass is then stirred for a period of fifteen minutes and heated to 70° C. The layers are separated and the organic layer is washed neutral (at 70° C.) with a 5% sodium hydroxide solution (two 250 ml volumes) and a 5% sodium chloride solution (three 250 ml volumes). 650 g of crude product is recovered and distilled after adding to the mixture 15 g of Primol ® and 0.2 g of Ionox ® through a 12" Vigreaux column as follows:

| Fraction | Vapor Temp. | Liquid Temp. | Vac. mm. | Weight of Fraction |
|---|---|---|---|---|
| 1 | 69 | 101/135 | 760/760 | 102.2 |
| 2 | 132 | 145 | 2.3 | 2.8 |
| 3 | 132 | 146 | 2.3 | 26.4 |
| 4 | 132 | 147 | 2.3 | 16.0 |
| 5 | 132/134 | 148/148 | 2.2/2.2 | 19.4 |
| 6 | 132 | 149 | 2.2 | 26.2 |
| 7 | 132 | 149 | 2.2 | 21.6 |
| 8 | 132 | 142 | 2.2 | 25.4 |
| 9 | 132 | 150 | 2.2 | 24.2 |
| 10 | 133 | 150 | 2.2 | 29.6 |
| 11 | 133 | 151 | 2.5 | 28.2 |
| 12 | 133 | 151 | 2.4 | 25.5 |
| 13 | 133 | 152 |  | 25.0 |
| 14 | 133 | 152 | 2.3 | 23.7 |
| 15 | 133 | 155 |  | 31.5 |
| 16 | 135 | 162 | 2.3 | 29.4 |
| 17 | 137 | 169 | 2.3 | 23.1 |
| 18 | 139 | 176 | 2.3 | 12.5 |
| 19 | 142 | 202 |  | 13.2 |
| 20 | 141 | 221 | 2.3 | 10.3 |

| Fraction | Vapor Temp. | Liquid Temp. | Vac. mm. | Weight of Fraction |
|---|---|---|---|---|
| 21 | 188 | 230 | | 10.5 |
| 22 | 187 | 242 | 2.3 | 8.1 |

FIG. 1 sets forth a GLC profile for Fraction 19. This fraction is primarily the alpha methyl styrene dimer having the structure:

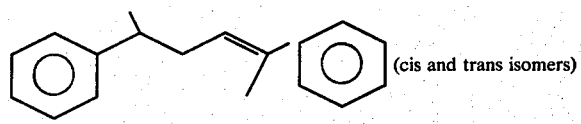

(cis and trans isomers)

Figure 2:
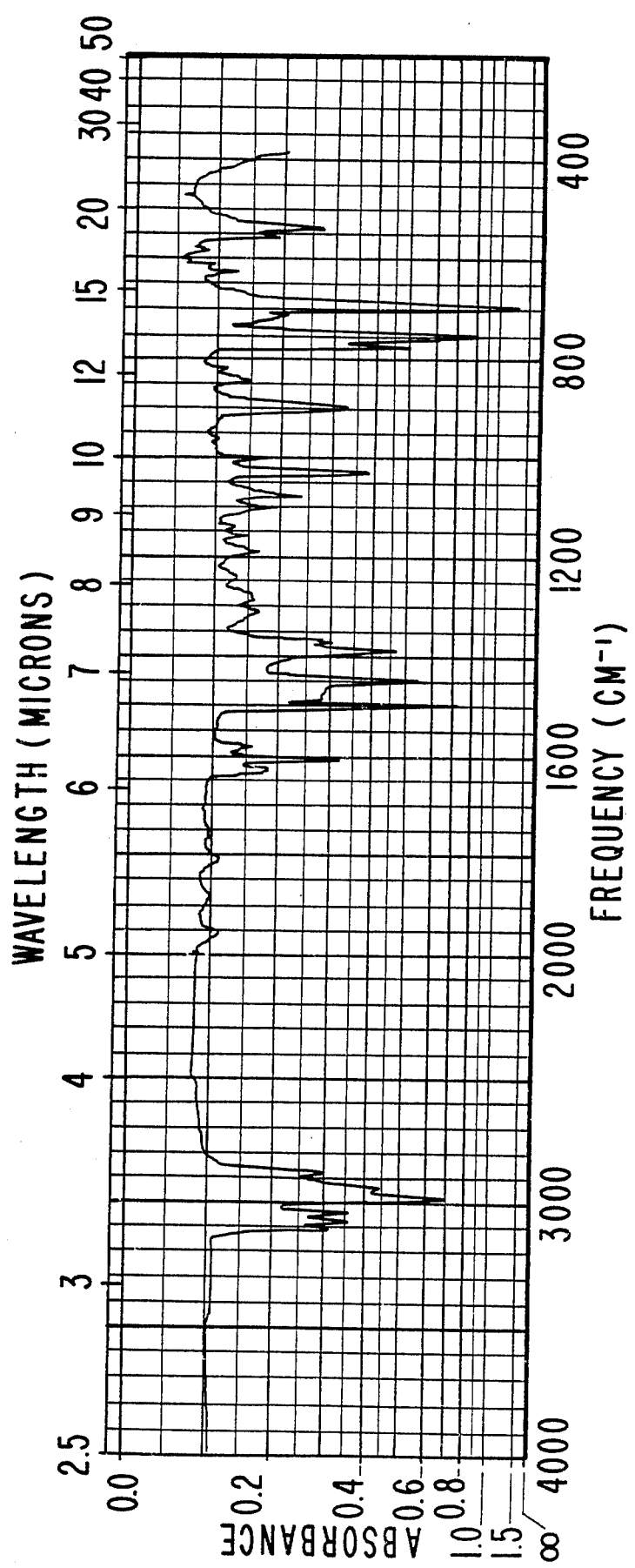
FIG. 2 is the infrared spectrum for the product produced according to Example I, Fraction 19.
Figure 3:
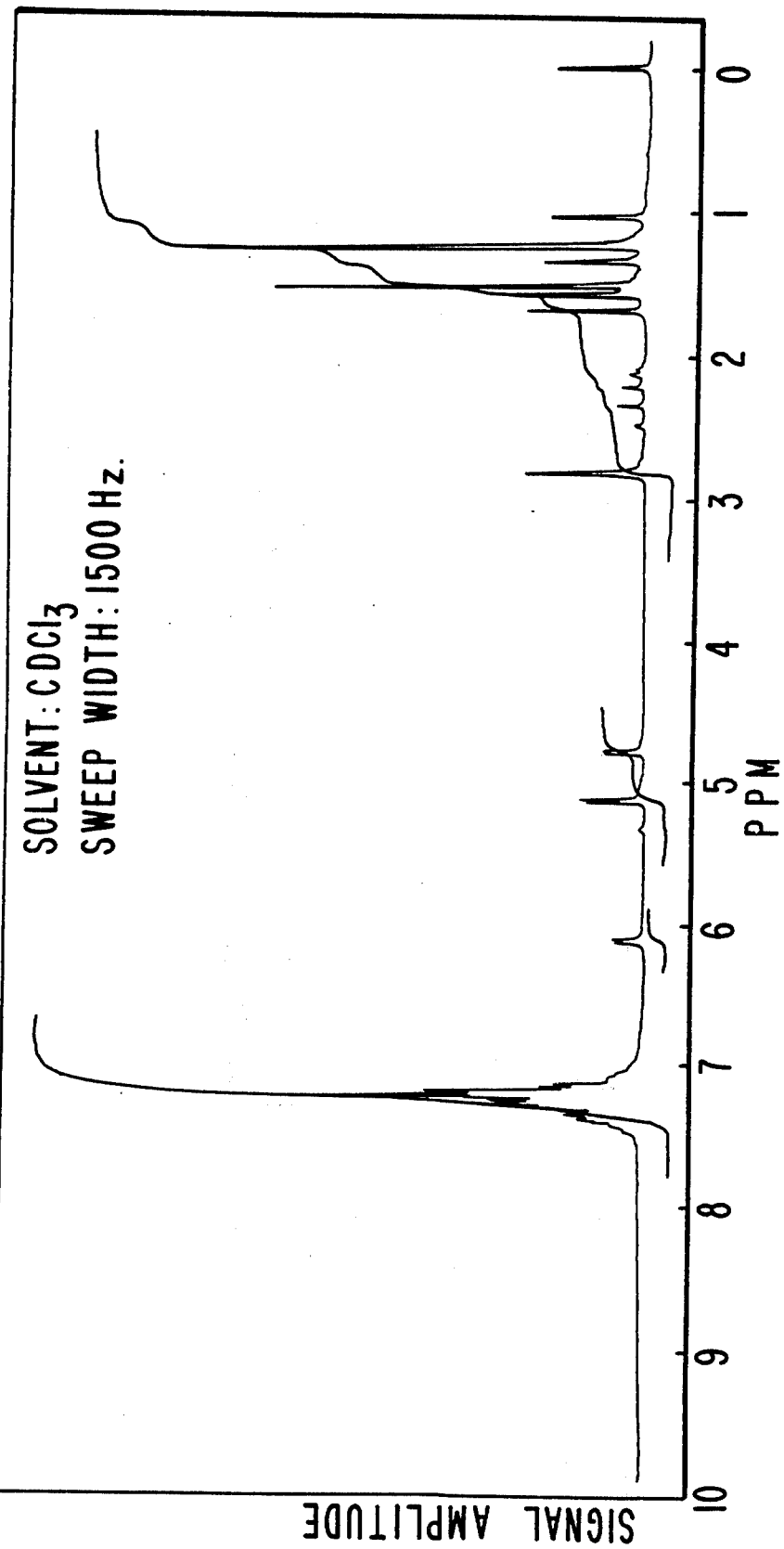
FIG. 3 is the NMR spectrum for the product produced according to Example I, Fraction 19.

FIG. 2 is the infrared spectrum for Fraction 19. FIG. 3 is the NMR spectrum for Fraction 19. The mass spectrum for Fraction 19 which is the compound having the structure:

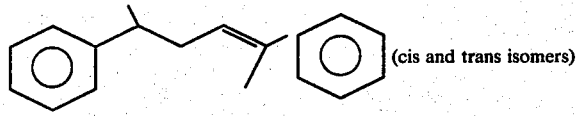

(cis and trans isomers)

is as follows:

| M/E | Relative Intensity |
|---|---|
| 39 | 23[5] |
| 41 | 27[4] |
| 51 | 18 |
| 77 | 19 |
| 91 | 42[2] |
| 103 | 14 |
| 119 | 100[1] |
| 143 | 20 |
| 221 | 32[3] |
| 236 | 20[6] |

Figure 4:
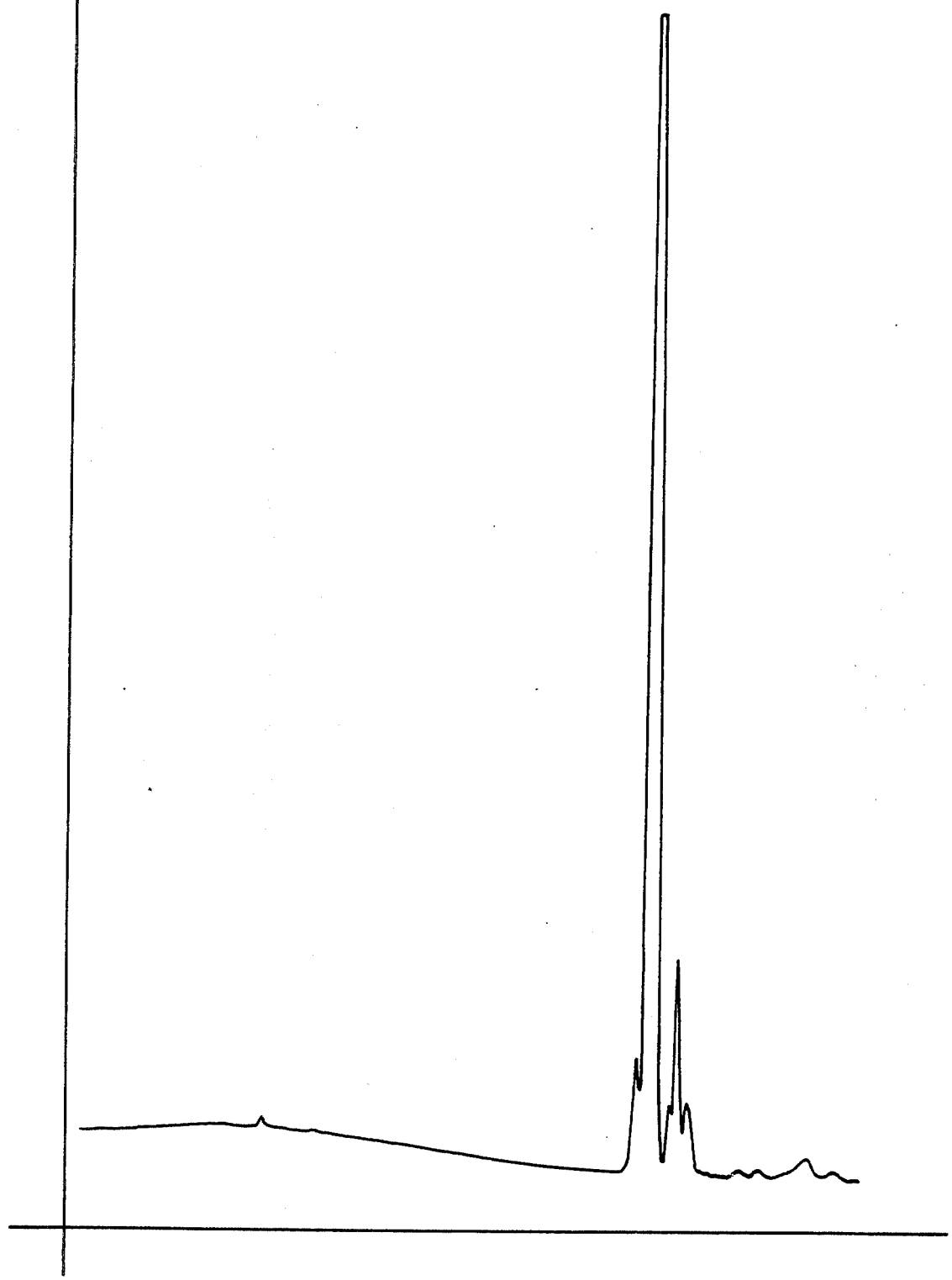
FIG. 4 is the GLC profile for the product produced according to Exmple I, Fraction 3.
Figure 5:
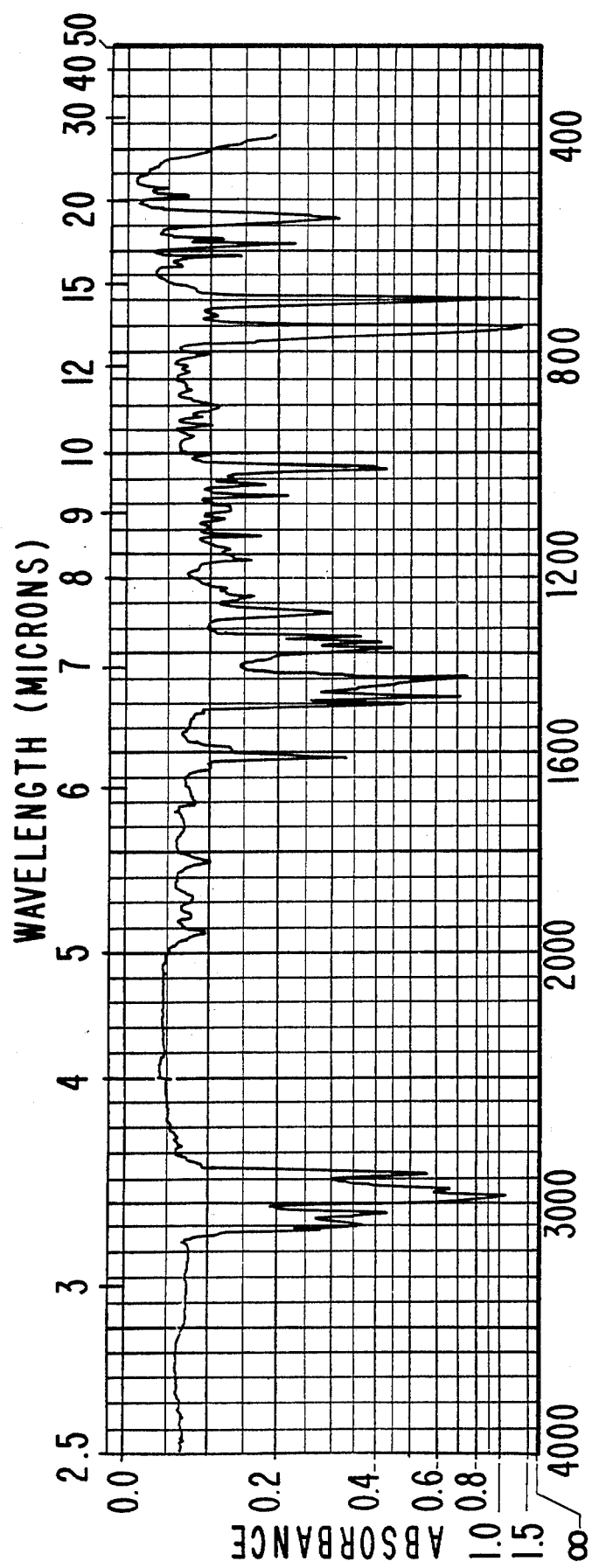
FIG. 5 is the infrared spectrum for the product produced according to Example I, Fraction 3 as well as Example III.
Figure 6:
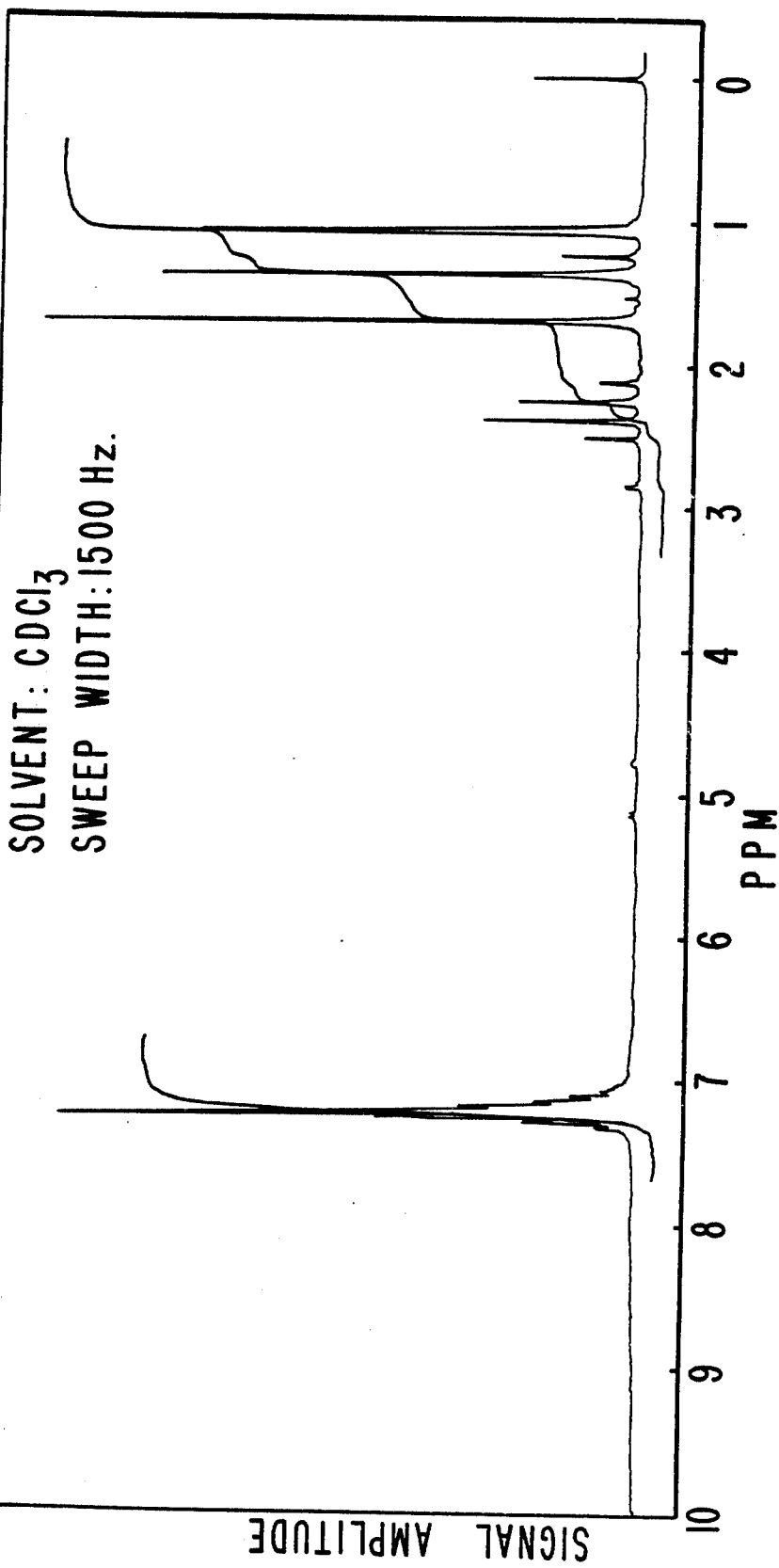
FIG. 6 is the NMR spectrum for the product produced according to Example I, Fraction 3 as well as the product produced according to Example III.

The GLC profile for Fraction 3 which is primarily the compound having the structure:

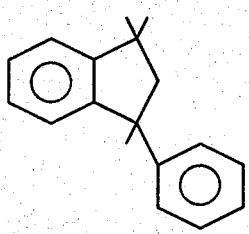

is set forth in FIG. 4. FIG. 5 sets forth the infrared spectrum for Fraction 3. FIG. 6 sets forth the NMR spectrum for Fraction 3.

FIGS. 4, 5 and 6 also represent, respectively, the GLC, IR and NMR spectrum for the product produced according to Example III, infra.

EXAMPLE II

PREPARATION OF ALPHA METHYL STYRENE DIMERIZATION PRODUCT

Reaction:

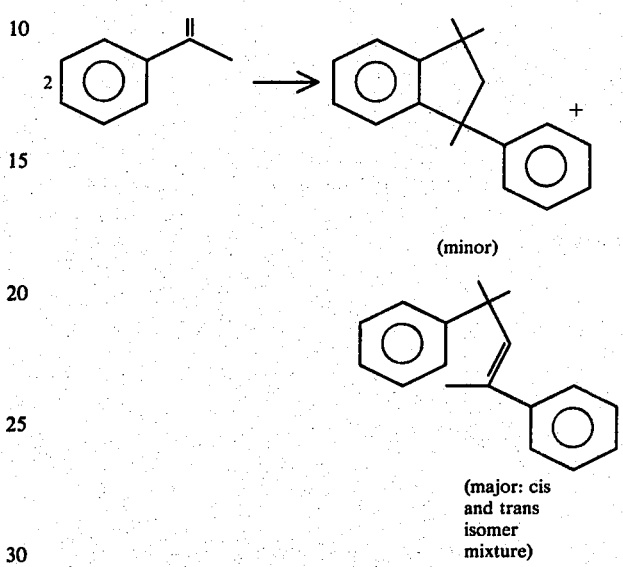

(minor)

(major: cis and trans isomer mixture)

Into a one-liter reaction flask equipped with thermometer, addition funnel, heating mantle, reflux condenser, stir, Y-adapter and distillation head is added 100 g of cyclohexane followed by 5 g of p-toluene sulfonic acid. The resulting mixture is heated to 50° C. and over a one hour period, 500 g of alpha methyl styrene is added to the reaction flask. The reaction mass is then heated to to 100° C. and maintained at that temperature for a period of four hours. 529.3 g of crude product is then recovered which is then mixed with 15 g of Primol ® and 0.2 g of Ionox ®. The resulting mixture is distilled through a "Y" adapter distillation column yielding the following distillation data:

| Fraction | Vapor Temp. | Liquid Temp. | Vac. mm. | Weight of Fraction |
|---|---|---|---|---|
| 1 | 21/80 | 90/149 | 2.6/2.5 | 6.4 |
| 2 | 139 | 155 | 2.5 | 7.0 |
| 3 | 139 | 155 | 2.5 | 21.4 |
| 4 | 140 | 157 | 2.5 | 34.0 |
| 5 | 142 | 160 | 2.4 | 49.6 |
| 6 | 144 | 170 | 2.4 | 100.4 |
| 7 | 164 | 195 | 2.4 | 58.5 |
| 8 | 174 | 203 | 2.2 | 8.0 |
| 9 | 200 | 215 | 3.5 | 70.0 |
| 10 | 202 | 215 | 2.2 | 31.3 |
| 11 | 206 | 215 | 2.2 | 27.1 |
| 12 | 214 | 225 | 2.2 | 18.1 |
| 13 | 210 | 250 | 2.2 | 41.6 |

EXAMPLE III

PREPARATION OF ALPHA METHYL STYRENE DIMER

Reaction:

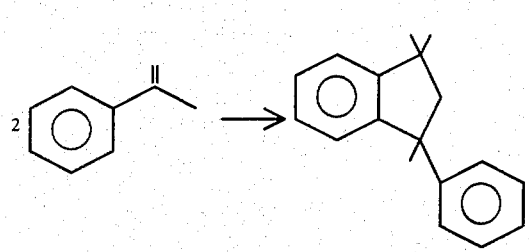

Into a 1,000 ml reaction flask equipped with thermometer, addition funnel, heating mantle, reflux conderser and stirrer is added 20 g of Filtrol 25 (a 10-20 mesh granular acid activated clay produced by the Filtrol Corporation of 5959 West Century Boulevard, Los Angles, Calif. 90045) having the following properties:

| Particle size analysis by Tyler Standard Sieve | | |
|---|---|---|
| Through 10 Mesh, Wt. % | 100 | |
| Through 20 Mesh, Wt. % | 5 | |
| Free Moisture, Wt. % | 10 | |
| Free and Combined Moisture, Wt. (Loss at 1700° F.) | 15 | (Max.) |
| Bulk Density, lbs./cu. ft. | 43.0 | |
| Particle Density | 1.3 | |
| Surface Area, $N_2$ adsorbent (Bet Method) $M^2$/gm 280-300 | | |

50 g of alpha methyl styrene is added to the Filtrol and the reaction mass is heated to 100° C. Another 450 g of alpha methyl styrene is then slowly added to the reaction mass over a period of two hours. The reaction mass is then heated to 150° C. and maintained at that temperature for a period of four hours. The reaction mass is then filtered yielding 470 g of crude product which is then mixed with 12 g Primol ® and 0.3 g Ionox ® and distilled through a 10" Vigreaux column, yielding the following fractions and the following distillation data:

| Fraction | Vapor Temp. | Liquid Temp. | Vac. mm. | Weight of Fraction (gm) |
|---|---|---|---|---|
| 1 | 38/88 | 135/140 | 2.5/2.5 | 1.2 |
| 2 | 133 | 142 | 2.0 | 7.0 |
| 3 | 134 | 142 | 2.0 | 12.0 |
| 4 | 134 | 142 | 2.0 | 17.1 |
| 5 | 134 | 145 | 1.8 | 53.5 |
| 6 | 134 | 146 | 1.8 | 31.0 |
| 7 | 135 | 147 | 1.8 | 49.2 |
| 8 | 135 | 148 | 1.8 | 51.5 |
| 9 | 136 | 149 | 1.8 | 46.2 |
| 10 | 137 | 151 | 1.8 | 52.3 |
| 11 | 137 | 159 | 1.8 | 43.2 |
| 12 | 139 | 170 | 1.8 | 17.5 |
| 13 | 185 | 225 | 1.8 | 21.6 |
| | | | | (Residue 40.3 g) |

Figure 7:
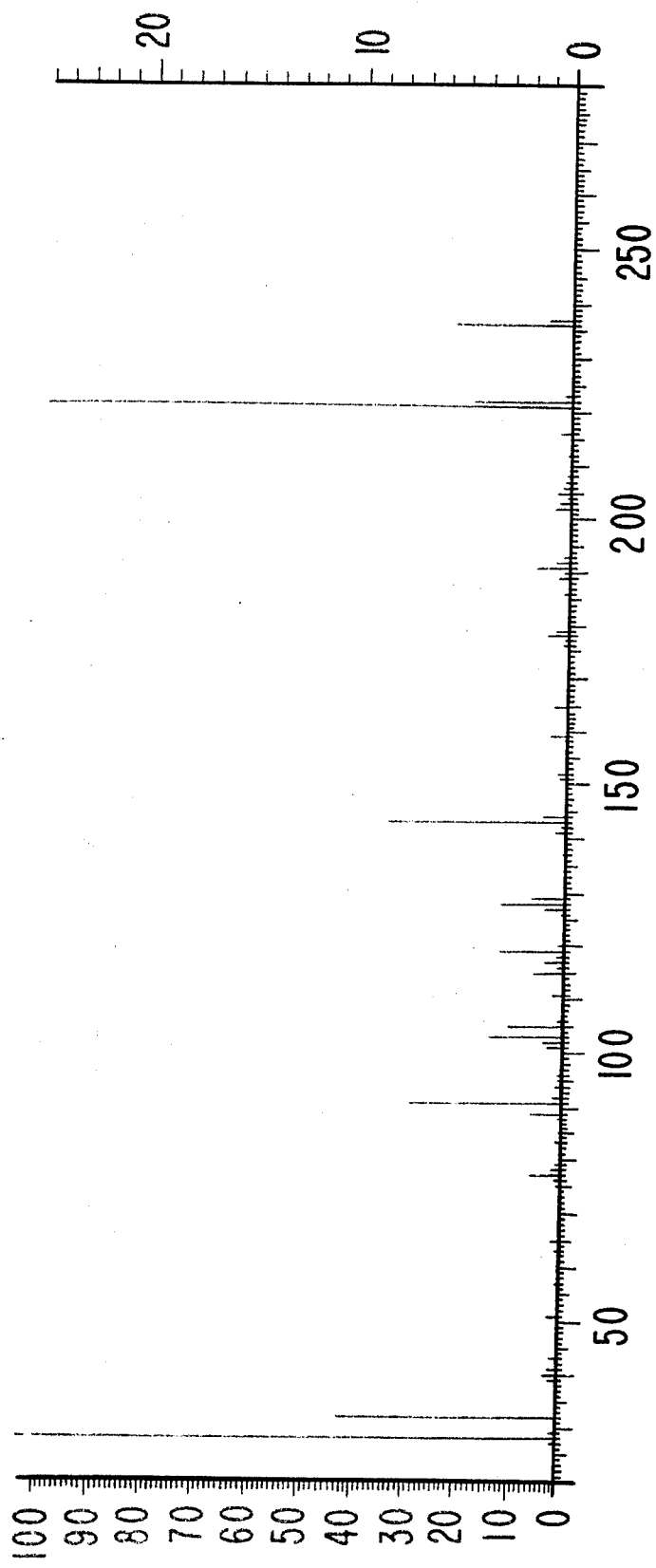
FIG. 7 is the mass spectrum for the product produced according to Example I, Fraction 3 as well as the product produced according to Example III.
Figure 8:
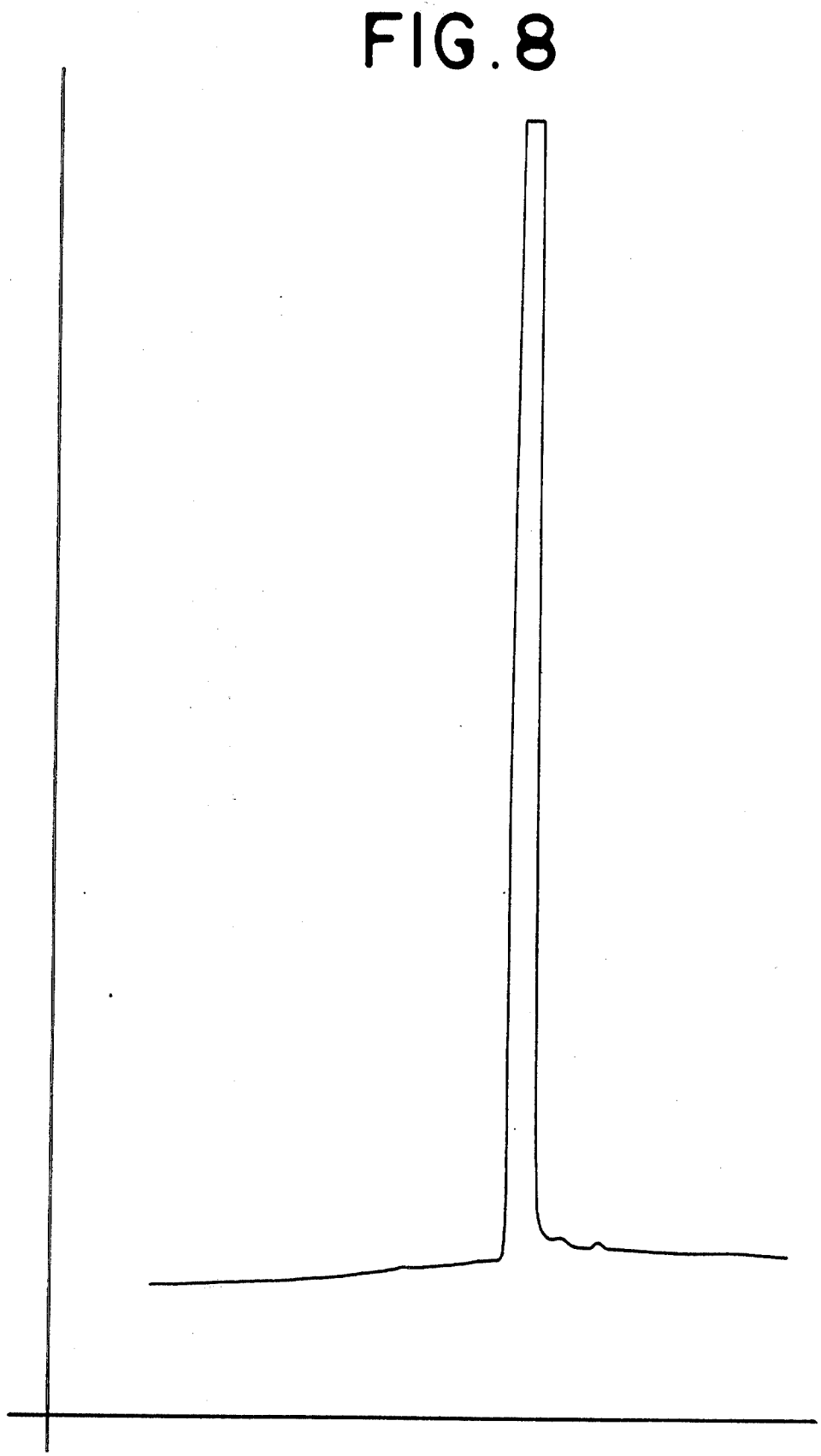
FIG. 8 is the GLC profile for the product produced according to Example III, Fractions 9–12 wherein a Filtrol[R] catalyst is used as the dimerizing agent.

FIG. 4 is the GLC profile for Fractions 9-12. FIG. 5 is the infrared spectrum for Fractions 9-12. FIG. 6 is the NMR spectrum for Fractions 9-12. FIG. 7 is the mass spectrum for Fractions 9-12. FIG. 8 is a second GLC profile for for Fractions 9-12.

EXAMPLE IV (A)

PREPARATION OF ALPHA PINENE DIMER

Reaction:

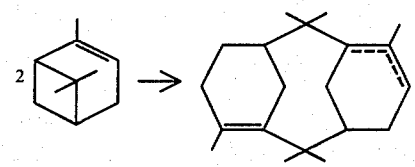

Into a two-liter reaction flask equipped with stirrer, thermometer, addition funnel and reflux condenser, are placed 100 g of alpha pinene and 40 g of Filtrol 25 (a 10-20 mesh granular acid activated clay produced by the Filtrol Corporation of 5959 West Century Boulevard, Los Angeles, Calif. 90045) having the following properties:

| Particle Size Analysis by Tyler Standard Sieve | | |
|---|---|---|
| Through 10 Mesh, Wt. % | 100 | |
| Through 20 Mesh, Wt. % | 5 | |
| Free Moisture, Wt. % | 10 | |
| Free and Combined Moisture, Wt. (Loss at 1700° F.) | 15 | (Max.) |
| Bulk Density, lbs./cu. ft. | 43.0 | |
| Particle Density | 1.3 | |
| Surface Area, $N_2$ adsorbent (Bet Method) $M^2$/gm 280-300 | | |

The reaction mass is heated to 150° C. with stirring and an additional 900 g of alpha pinene is added thereto over a period of two hours while maintaining the reaction mass at 150° C. The reaction mass is then continued to be stirred at 150° C. until GLC analysis of sampler shows that the reaction is complete (whereby little or no alpha pinene remains).

The reaction mass is then cooled to 80° C. and filtered using filter cell.

The filtrate is distilled at 3 mm Hg. vacuum using a 12 inch Goodloe column and starting at a 9:1 reflux ratio and then going to 4:1. Just prior to distillation, 30 g of Primol ® is added to the material to be distilled. The distillation data are as follows:

| Fraction | Vapor Temp. | Liquid Temp. | Vac. mm. | Reflux Ratio | Weight of Fraction |
|---|---|---|---|---|---|
| 1 | 35/75 | 72/115 | 50/35 | 9:1/9:1 | 44.1 |
| 2 | 39 | 95 | 3.0 | 9:1 | 53.9 |
| 3 | 41 | 103 | 3.0 | 9:1 | 46.0 |
| 4 | 41 | 165 | 3.0 | 4:1 | 68.7 |
| 5 | 31/128 | 152/168 | 1.0/.8 | 4:1/4:1 | 38.0 |
| 6 | 133 | 175 | 0.8 | 4:1 | 43.0 |
| 7 | 133 | 179 | 0.8 | 4:1 | 51.1 |
| 8 | 133 | 180 | 0.8 | 4:1 | 49.4 |
| 9 | 133 | 181 | 0.8 | 4:1 | 44.5 |
| 10 | 133 | 185 | 0.8 | 4:1 | 49.5 |
| 11 | 133 | 187 | 0.8 | 4:1 | 47.5 |
| 12 | 136 | 193 | 0.8 | 4:1 | 42.7 |
| 13 | 140 | 204 | 0.8 | 4:1 | 44.5 |

Figure 9:
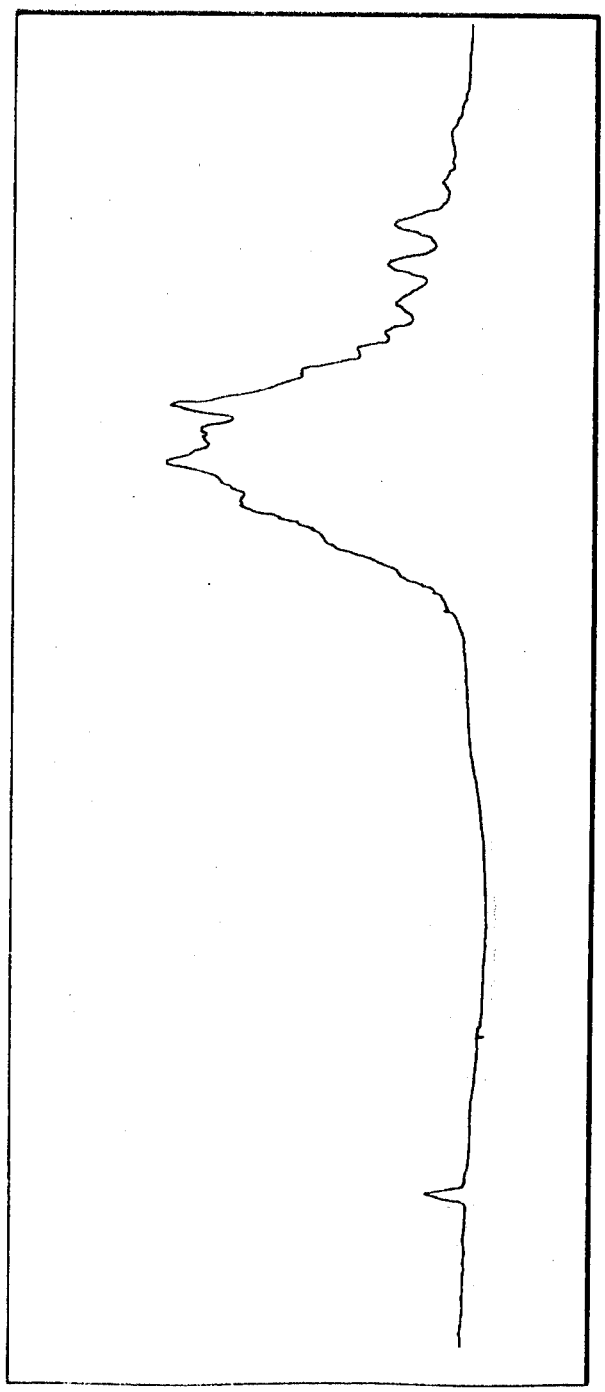
FIG. 9 is the GLC profile for the dimerization product of alpha-pinene produced according to Example IV (A).

FIG. 9 is the GLC profile for the alpha pinene dimer (fractions 9-11). (Conditions: 2% Carbowax Column, 25'×¼" programmed at 80°-220° C. at 10° C. per minute).

Figure 11:
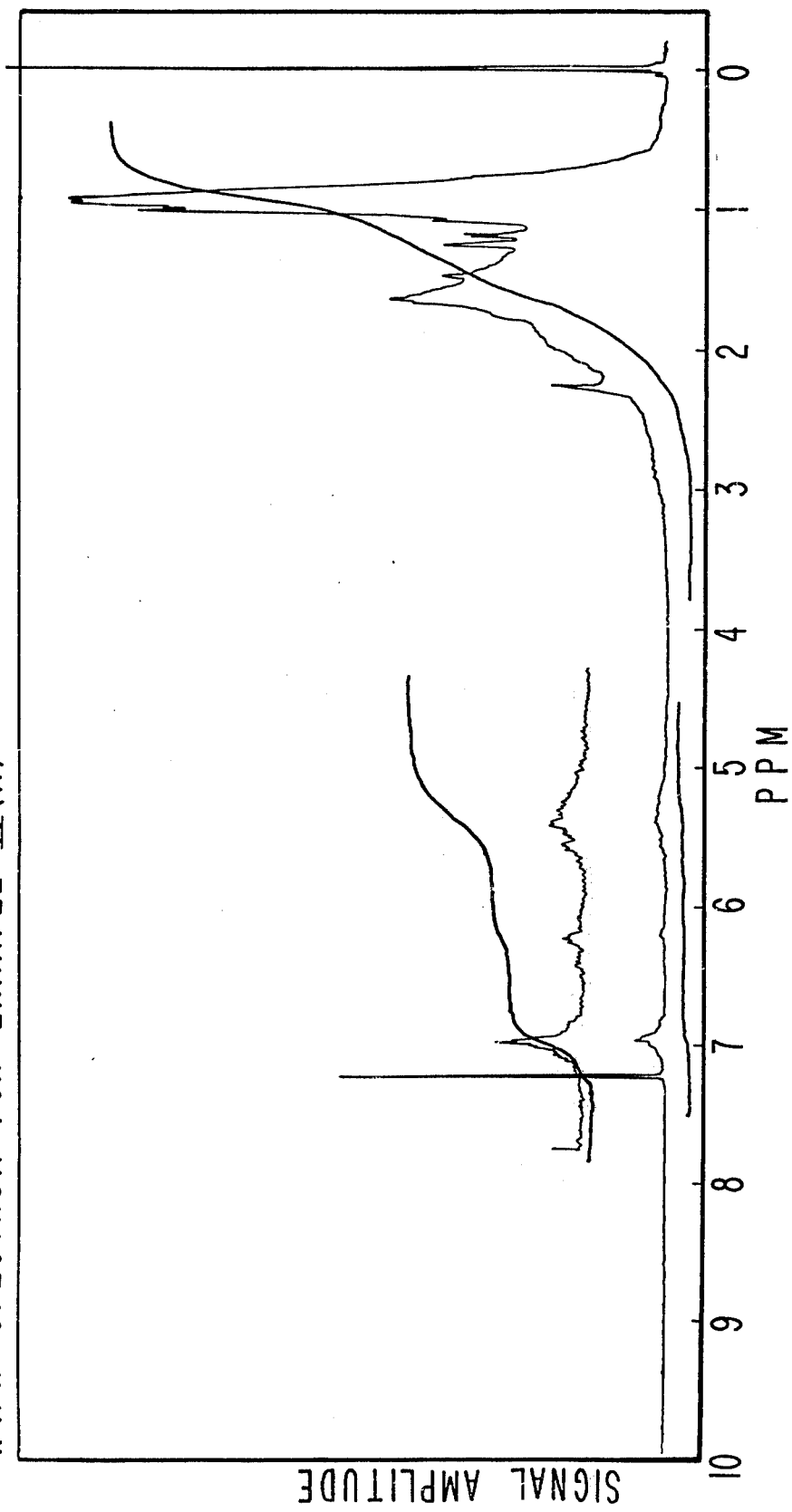
FIG. 11 is the NMR spectrum for the product produced according to Example IV (A).
Figure 12:
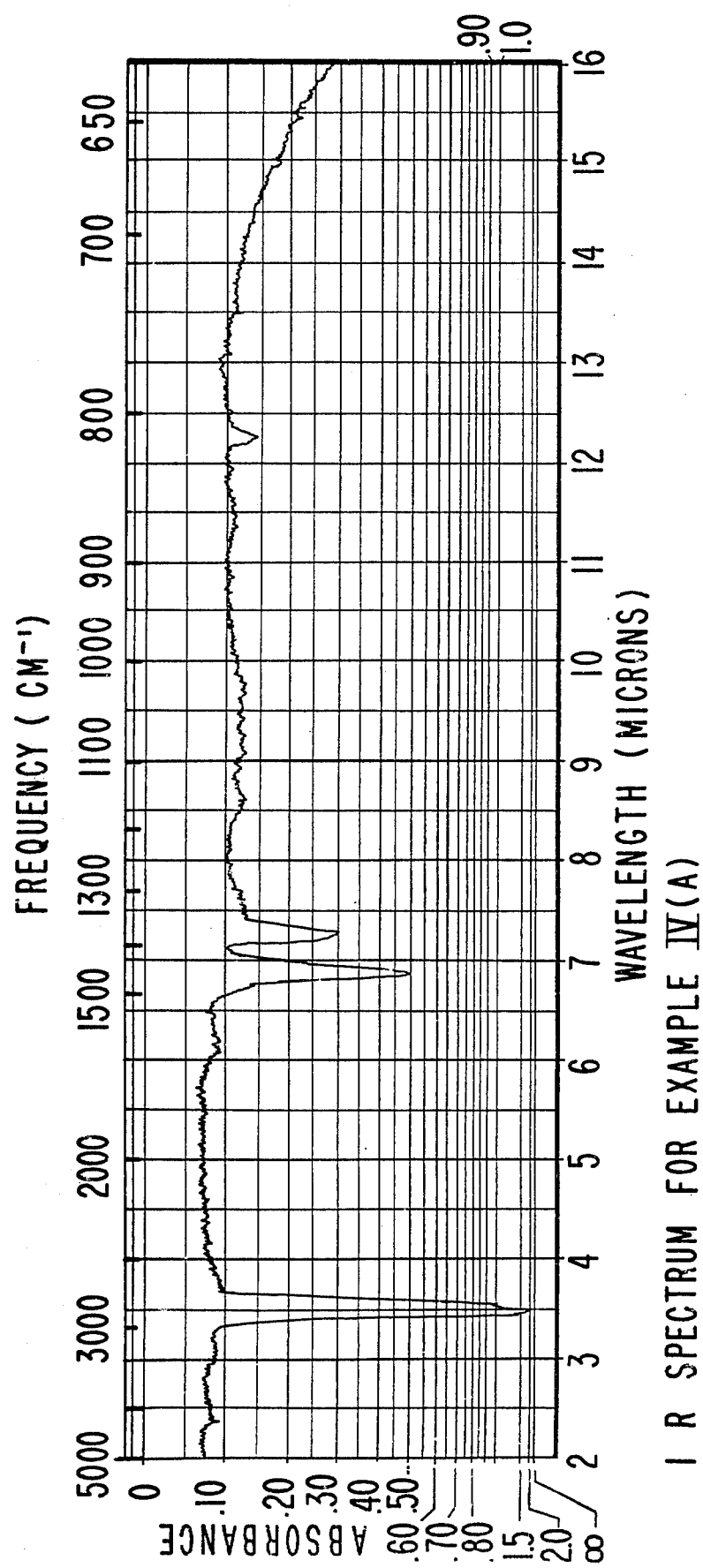
FIG. 12 is the infrared spectrum for the product produced according to Example IV (A).

FIG. 11 is the NMR spectrum for the product of Example IV (A). FIG. 12 is the IR spectrum for the product of Example IV (A).

EXAMPLE IV (B)

DIMERS OF CAMPHENE

Into a two-liter reaction flask equipped with stir, thermometer, addition funnel and reflux condenser with Bidwell Trap are placed:

| | |
|---|---|
| Hexahydropentamethylindane | 336 g |
| Filtrol 25 (Properties set forth in Example I (A) | 32 g | with stirring the mixture is heated to 155° C. Over a period of 2.25 hours while maintaining the reaction mass at 155° C., 547 g of Camphene is added thereto. The reaction mass is then stirred for 7½ hours at 155°/158° C. and progress of dimerization is monitored on GLC apparatus (Conditions: 5% SE 30 column, 10′×¼″, programmed at 80°-240° C. at 8° C. per minute). GLC analysis shows very little change after 2 hours. The reaction mass is then filtered. The filter cake is washed with 200 g of hexahydropentamethylindane. The weight of filtrate is 1056 grams. The resultant filtrate is distilled in the presence of Primol ® (30 g) and Ionox ® (1 g) through an 18″ Vigreux column equipped with reflux head. The following distillation data is obtained:

| Fraction No. | Vapor Temp. °C. | Pot Temp. °C. | Pressure mm Hg. | Weight of Fraction (Grams) | GLC Analysis of Fraction |
|---|---|---|---|---|---|
| 1-6 | 45-100 | 87-160 | 2.6 | 631.9 | Recovered hexahydropentamethyl-indane |
| 7 | 149 | 170 | 3.5 | 10.5 | Intermediate Section |
| 8 | 150 | 170 | 2.8 | 40.7 | Practically Pure Dimers |
| 9-11 | 152-168 | 176-230 | 2.5 | 214.8 | Pure Dimers |
| 12 | 215 | 275 | 2.5 | 22.9 | |
| 13-14 | 225-250 | 290-306 | 2.5 | 62.7 | Very Little Eluted on GLC |
| | | | Residue - | 41.7 | |
| | | | Trap - | 18.0 | |

Figure 10:
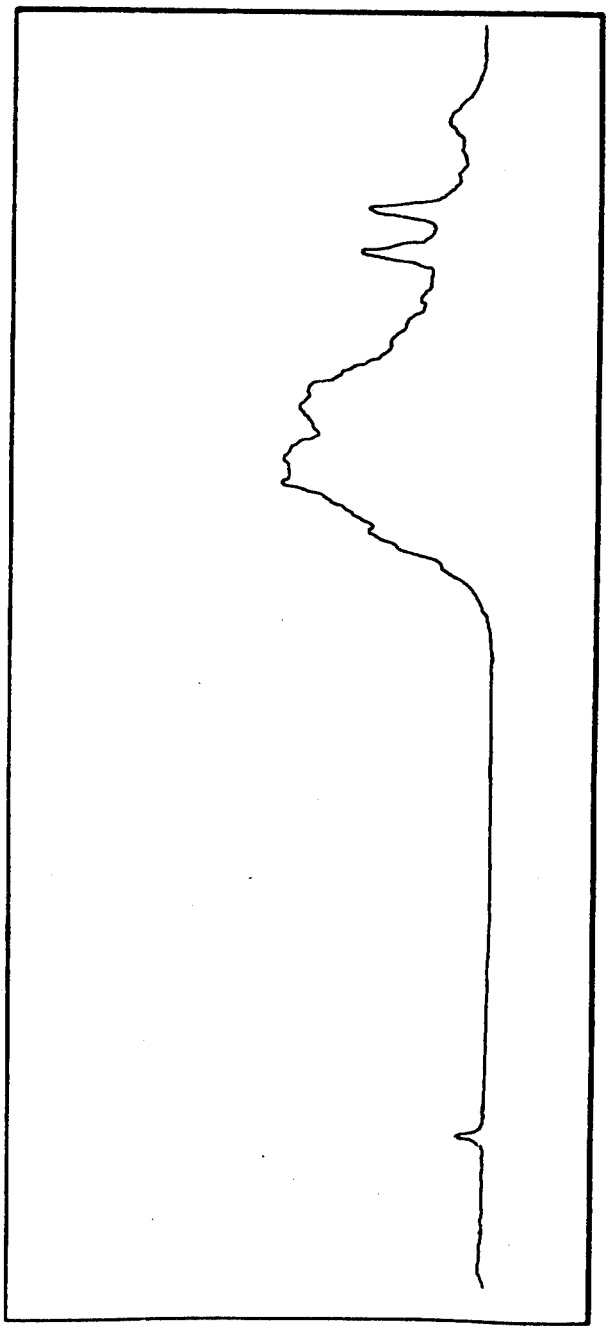
FIG. 10 is the GLC profile for the dimerization product of camphene produced according to Example IV (B).

FIG. 10 sets forth the GLC profile for fractions 9-11, the camphene dimer (Conditions: 5% SE 30 column, 10′×¼″, programmed at 80°-240° C. at 8° C. per minute).

The structure of the hexahydropentamethylindane, used as a solvent is as follows:

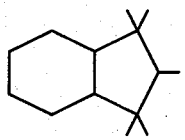

EXAMPLE IV (C)

PREPARATION OF d-LIMONENE DIMER

Into a 500 ml reaction flask equipped with thermometer, stirrer, condenser and addition funnel are placed 5 g Primol ® and 2 g Filtrol 25. The reaction mixture is heated to 150° C. and 40 g of limonene is added dropwise over a period of 80 minutes. The reaction mass is then heated at 150° C. for 3 hours.

The reaction mass is then cooled, filtered and distilled. The resulting product is the dimer of d-limonene, confirmed by GLC, NMR and IR analyses.

Figure 13:
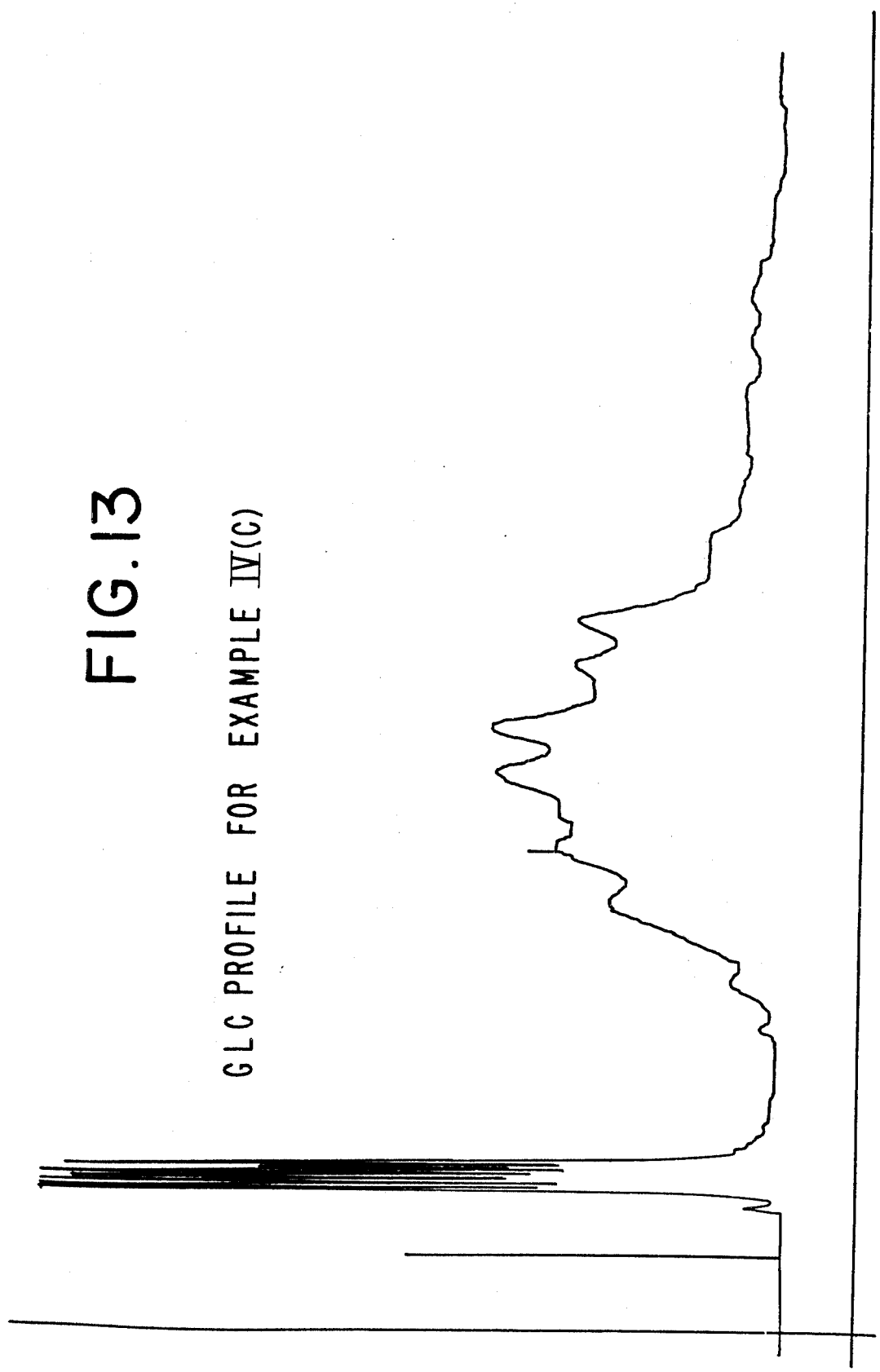
FIG. 13 is the GLC profile for the product produced according to Example IV (C), the dimerization product of limonene.
Figure 14:
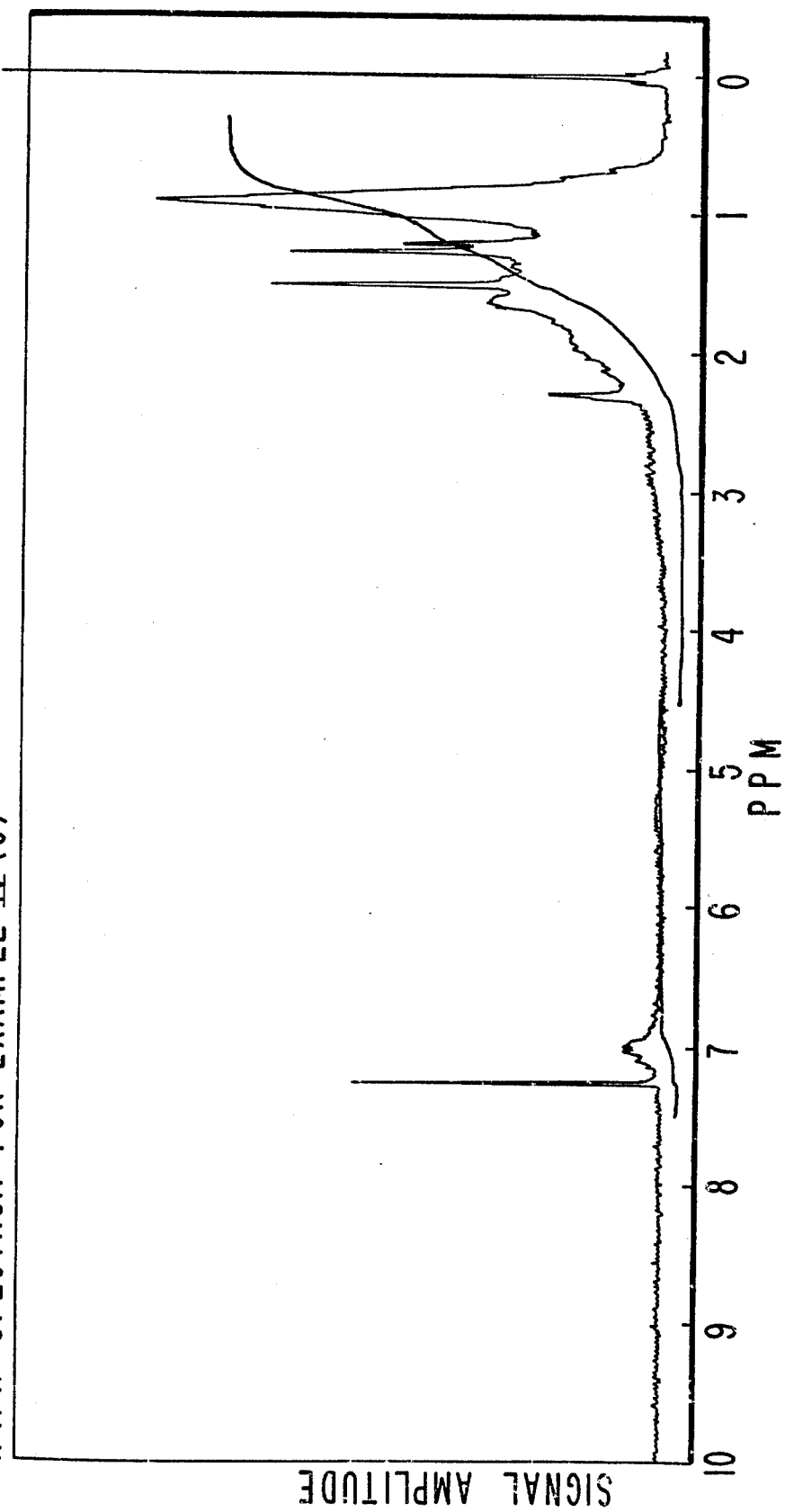
FIG. 14 is the NMR spectrum for the product produced according to Example IV (C), the dimer of limonene.

The GLC profile is set forth in FIG. 13. The NMR spectrum is set forth in FIG. 14. The IR spectrum is set forth in FIG. 15.

EXAMPLE V

Patchouli oil (80 parts) obtained from the Seychelle Islands is blended with 10 parts of the alpha methyl styrene dimer produced according to any one of Examples I, II or III and 10 parts of the alpha pinene dimer of Example IV (A). The alpha methyl styrene dimer—alpha pinene dimer mixture is found to act as an extender for the patchouli oil in that the characteristic odor effect of the latter is substantially not modified.

EXAMPLE VI

The extended patchouli oil prepared according to Example V is successfully incorporated into a compounded composition of the Chypre type by blending the following ingredients:

| | Parts |
|---|---|
| Cinnamic Aldehyde | 1 |
| Ethyl Methyl Phenyl Glycidate | 1 |
| Methyl Nonyl Acetaldehyde | 2 |
| Oakmoss (Absolute) | 20 |
| Sandalwood Oil (East Indian) | 20 |
| Vetiveryl Acetate | 20 |
| Ylang Oil No. 1 | 20 |
| Benzoin Resoin (Sumatra) | 30 |
| Alpha Ionone (100%) | 30 |
| Clove Stem Oil (Zanzibar) | 36 |
| Bergamot Oil | 40 |
| Hydroxycitronellal | 40 |
| Iso Eugenol | 40 |
| Extended Patchouli Oil (Example V) | 40 |
| Coumarin | 50 |
| Musk Ketone | 50 |
| Amyl Salicylate | 60 |
| Cedarwood Oil (American) | 60 |
| Citronellol | 60 |
| Benzyl Acetate | 80 |
| Phenyl Ethyl Alcohol | 150 |
| Terpinyl Acetate | 150 |
| | 1000 |

EXAMPLE VII

A patchouli oil extender base is prepared by blending the following ingredients:

| | Parts |
|---|---|
| Mixture of 10 parts of alpha methyl styrene dimer produced according to any one of Examples I, II or III and 28 parts of d-limonene dimer produced according to | 38 |

| | Parts |
|---|---|
| Example IV (C) | |
| Galaxolide | 27 |
| Isolongifolene Oxidate | 20 |
| Omega-Hydroxymethyl Longifolene | 10 |
| Cedrol | 3 |
| Sandalwood Oil (East Indian) | 2 |
| | 100 |

This mixture (46 parts) is then blended with natural patchouli oil (Seychelles) (60 parts) to provide a satisfactory extended patchouli oil.

EXAMPLE VIII

The extended patchouli oil prepared in Example VII is incorporated into a compounded perfumery composition of the Fougere type containing the following ingredients:

| | Parts |
|---|---|
| Balsam Peru | 30 |
| Labdanum Resin | 30 |
| Oakmoss Absolute | 30 |
| Sandalwood Oil (East Indian) | 30 |
| Linalyl Acetate | 40 |
| Terpinyl Acetate | 40 |
| Geranium Oil (Bourbon) | 50 |
| Musk Ambrette | 50 |
| Coumarin | 60 |
| Amyl Salicylate | 60 |
| Methyl Ionone | 70 |
| Cedarwood Oil (American) | 80 |
| Clove Stem Oil (Zanzibar) | 80 |
| Vetivert Oil (Bourbon) | 80 |
| Extended Patchouli Oil | 130 |
| Lavandin Oil | 140 |
| | 1000 |

EXAMPLE IX

Patchouli oil (85 parts) obtained from the Seychelle Islands is blended with the 10 parts by weight camphene dimer produced according to Example IV (B) and 5 parts of the alpha methyl styrene dimer of Example II. The camphene dimer—alpha methyl styrene dimer mixture is found to act as an extender for the patchouli oil in that the characteristic odor effect of the latter is substantially not modified.

EXAMPLE X

The extended patchouli oil prepared according to Example IX is successfully incorporated into a compounded composition of the Chypre type by blending the following ingredients:

| | Parts |
|---|---|
| Cinnamic Aldehyde | 1 |
| Ethyl Methyl Phenyl Glycidate | 1 |
| Methyl Nonyl Acetaldehyde | 2 |
| Oakmoss (Absolute) | 20 |
| Sandalwood Oil (East Indian) | 20 |
| Vetiveryl Acetate | 20 |
| Ylang Oil No. 1 | 20 |
| Benzoin Resoin (Sumatra) | 30 |
| Alpha Ionone (100%) | 30 |
| Clove Stem Oil (Zanzibar) | 36 |
| Bergamot Oil | 40 |
| Hydroxycitronellal | 40 |
| Iso Eugenol | 40 |
| Extended Patchouli Oil | 40 |

| | Parts |
|---|---|
| (Example IX) | |
| Coumarin | 50 |
| Musk Ketone | 50 |
| Amyl Salicylate | 60 |
| Cedarwood Oil (American) | 60 |
| Citronellol | 60 |
| Benzyl Acetate | 80 |
| Phenyl Ethyl Alcohol | 150 |
| Terpinyl Acetate | 150 |
| | 1000 |

What is claimed is:

1. A mixture of (A) a dimerization product of an α-methyl styrene or a methyl or other $C_2$-$C_4$ lower alkyl homologue thereof or mixture of same having one of the generic structures:

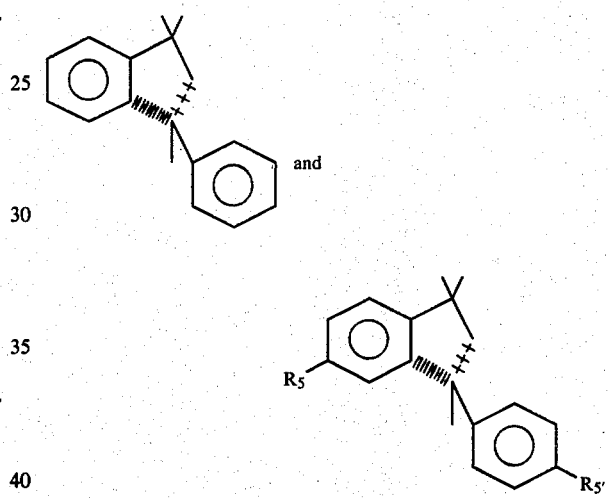

or hydrogenated derivatives thereof or mixtures of the foregoing wherein one $R_5$ and $R_5'$ is $C_1$-$C_4$ alkyl and the other of $R_5$ and $R_5'$ is hydrogen or $R_5$ and $R_5'$ are both $C_1$-$C_4$ alkyl; wherein the line | | | | represents a carbon-carbon single bond or no bond and wherein the line, + + + + + +, represents a carbon-carbon single bond or a carbon-carbon double bond, with the proviso that when the line + + + + is a carbon-carbon double bond then the line | | | | is no bond and when the line + + + + is a carbon-carbon single bond then the line | | | | is a carbon-carbon single bond, said hydrogenated alpha methyl styrene dimerization product having at least one structure defined according to at least one of the generic structures selected from the group consisting of:

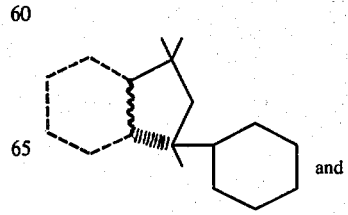

and

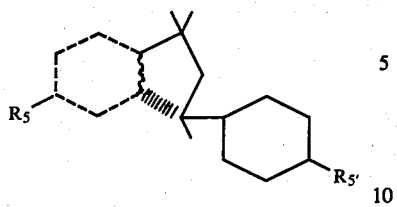

wherein one of R₅ and R₅' is $C_1$-$C_4$ alkyl and the other is hydrogen or each of R₅ and R₅' is $C_1$-$C_4$ alkyl; wherein the dashed lines and the wavy line represent carbon-carbon single bonds or carbon-carbon double bonds with the proviso that when there is one double bond present in the ring having a wavy line and dashed lines, only the wavy line is a double bond and when there is more than one double bond present in the ring containing the dashed lines and the wavy line, the ring containing the dashed lines and the wavy line is a benzene ring; and wherein the line ||| represents either a carbon-carbon single bond or no bond and (B) a reaction product selected from the group consisting of (I) one or more twenty carbon atom containing dimerization products of (i) one monocyclic terpene containing two carbon-carbon double bonds or (ii) two different monocyclic terpenes containing two carbon-carbon double bonds or (iii) one bicyclic terpene containing one carbon-carbon double bond or (iv) two different bicyclic terpenes, each containing one carbon-carbon double bond or (v) one monocyclic terpene containing two carbon-carbon double bonds and one bicyclic terpene containing one carbon-carbon double bond; (II) hydrogenation products of one or more twenty carbon atom containing dimerization products of twenty carbon atom-containing terpenes and one or more hydrogenation products of one or more twenty carbon atom containing dimerization products of terpenes.

2. The mixture of claim 1 wherein the dimerization product (A) is an α-methyl styrene dimer having the structure:

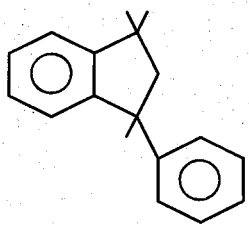

3. The mixture of claim 1 wherein the dimerization product (A) is a hydrogenated dimerization product having at least one structure selected from the group consisting of:

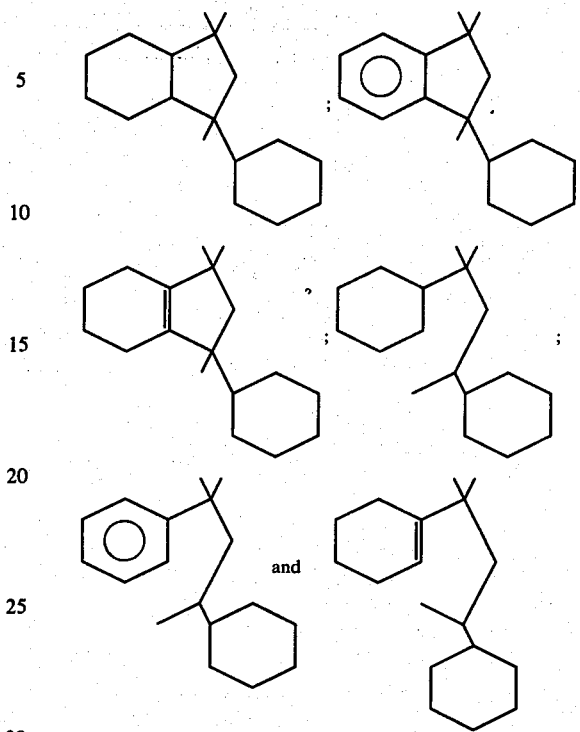

4. The mixture of claim 1 wherein the reaction product (B) is a dimerization product selected from the group consisting of:
Dimerization products of α-pinene;
Dimerization products of β-pinene;
Dimerization products of camphene;
Dimerization products of d-limonene;
Dimerization products of turpentine;
Hydrogenated dimerization products of α-pinene;
Hydrogenated dimerization products of β-pinene;
Hydrogenated dimerization products of camphene;
Hydrogenated dimerization products of d-limonene;
Hydrogenated dimerization products of turpentine;
Mixtures of said dimerization products; and
Mixtures of said hydrogenated dimerization products.

5. The mixture of claim 4 wherein the reaction product (B) is a dimerization product and said dimerization product is the dimerization product of α-pinene.

6. The mixture of claim 4 wherein the reaction product (B) is a dimerization product and the dimerization product is the dimerization product of camphene.

7. The mixture of claim 4 wherein the reaction product (B) is a dimerization product and the dimerization product is the dimerization product of d-limonene.

8. The mixture of claim 4 wherein the reaction product (B) is a dimerization product and the dimerization product is the dimerzation product of turpentine.

9. A single phase liquid compounded perfumery composition which comprises at least one natural perfumery oil, synthetic perfumery oil or synthetic perfumery chemical or a mixture of natural perfumery oils and synthetic perfumery oils or a mixture of ntural perfumery oils and synthetic perfumery chemicals or a mixture of synthetic perfumery oils and synthetic perfumery chemicals with which there is intimately admixed from about 1 up to about 30 parts by weight of at least one odorless perfumery extender which is a mixture defined according to claim 1 per 100 parts by weight of said compounded single phase liquid perfumery composition.

10. The compounded perfumery composition of claim 9 wherein the dimerization product (A) is an α-methyl styrene dimer having the structure:

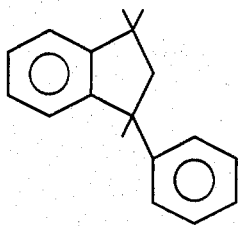

11. The compounded perfumery composition of claim 9 wherein the dimerization product (A) is a hydrogenated dimerization product having at least one structure selected from the group consisting of:

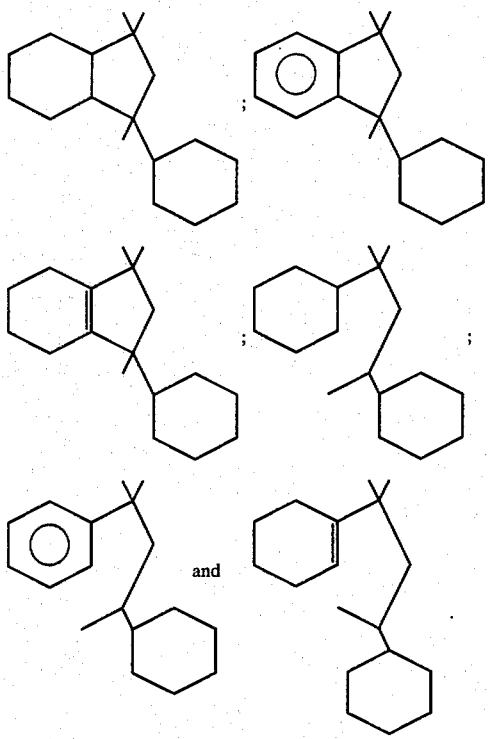

12. The compounded single phase liquid perfumery composition of claim 9 wherein the reaction product (B) is a dimerization product selected from the group consisting of:

Dimerization products of α-pinene;
Dimerization products of β-pinene;
Dimerization products of camphene;
Dimerization products of d-limonene;
Dimerization products of turpentine;
Hydrogenated dimerization products of α-pinene;
Hydrogenated dimerization products of β-pinene;
Hydrogenated dimerization products of camphene;
Hydrogenated dimerization products of d-limonene;
Hydrogenated dimerization products of turpentine;
Mixtures of said dimerization products; and
Mixtures of said hydrogenated dimerization products.

13. The compounded single phase liquid perfumery composition of claim 12 wherein the reaction product (B) is a dimerization product and said dimerization product is the dimerization product of α-pinene.

14. The compounded single phase liquid perfumery composition of claim 12 wherein the reaction product (B) is a dimerization product and the dimerization product is the dimerization product of camphene.

15. The compounded single phase liquid perfumery composition of claim 12 wherein the reaction product (B) is a dimerization product and the dimerization product is the dimerization product of d-limonene.

16. The compounded single phase liquid perfumery composition of claim 12 wherein the reaction product (B) is a dimerization product and the dimerization product is the dimerization product of turpentine.

17. A process for extending a perfumery product selected from the group consisting of natural perfumery oils, synthetic perfumery oils, synthetic perfumery chemicals, mixtures of natural perfumery oils and synthetic perfumery oils, mixtures of natural perfumery oils, synthetic perfumery oils and synthetic perfumery chemicals and mixtures of synthetic perfumery oils and synthetic perfumery chemicals without substantially altering the aroma thereof which comprises intimately admixing from about 1 up to about 30 parts by weight of a mixture of (A) one or more dimerization products selected from the group consisting of α-methyl styrene dimerization products and hydrogenated α-methyl styrene dimerization products, said α-methyl styrene dimerization products being defined by at least one generic structure selected from the group consisting of:

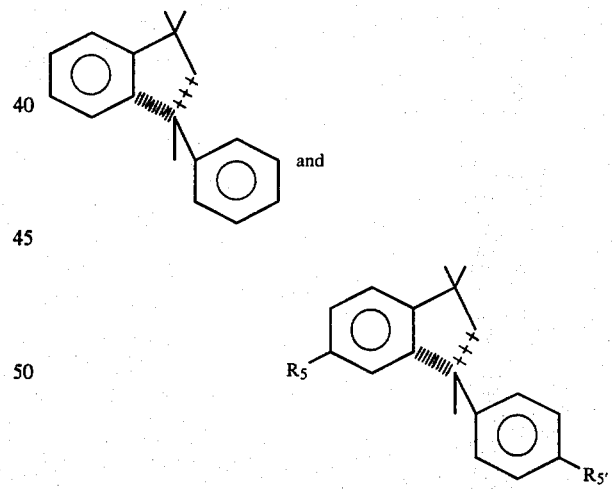

wherein one of $R_5$ and $R_5'$ is $C_1$-$C_4$ alkyl and the other of $R_5$ and $R_5'$ is hydrogen or $R_5$ and $R_5'$ are both $C_1$-$C_4$ alkyl; wherein the line, | | | | represents a carbon-carbon single bond or no bond and wherein the line, + + + + + represents a carbon-carbon single bond or a carbon-carbon double bond, with the proviso that when the line + + + + + is a carbon-carbon double bond then the line | | | | is no bond and when the line + + + + + is a carbon-carbon single bond then the line | | | | is a carbon-carbon single bond, and said hydrogenated alpha methyl styrene dimerization product having at least one structure defined according to at least one of the generic structures selected from the group consisting of:

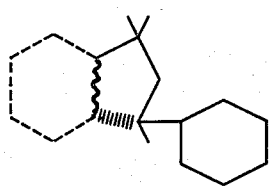
and

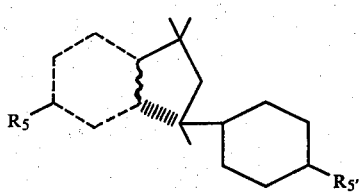

wherein one or $R_5$ and $R_5'$ is $C_1$–$C_4$ alkyl and the other is hydrogen or each of $R_5$ and $R_5'$ is $C_1$–$C_4$ alkyl; wherein the dashed lines and the wavy line represent carbon-carbon single bonds or carbon-carbon double bonds with the proviso that when there is one double bond present in the ring having a wavy line and dashed lines, only the wavy line is a double bond and when there is more than one double bond present in the ring containing the dashed lines and the wavy line, the ring containing the dashed lines and the wavy line is a benzene ring; and wherein the line | | | | represents either a carbon-carbon single bond or no bond and (B) a reaction product selected from the group consisting of (I) dimerization products of (i) the same or different monocyclic ten carbon atom-containing terpenes containing two carbon-carbon double bonds, or (ii) the same or different bicyclic ten carbon atom-containing terpenes containing one carbon-carbon double bond, or (iii) a monocyclic terpene containing two carbon-carbon double bonds and a bicyclic terpene containing one carbon-carbon double bond and (II) hydrogenation products of said dimerization product, with from 70 up to 99 parts by weight of said perfumery product.

18. The process of claim 17 wherein the reaction product is a dimerization product and the dimerization product is the dimerization product of camphene.

19. The process of claim 18 wherein the dimerzation product (A) is an α-methyl styrene dimerization product defined according to the structure:

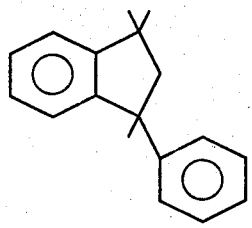

20. The process of claim 18 wherein the dimerization product (A) is a hydrogenated dimerization product of α-methyl styrene having a structure selected from the group consisting of:

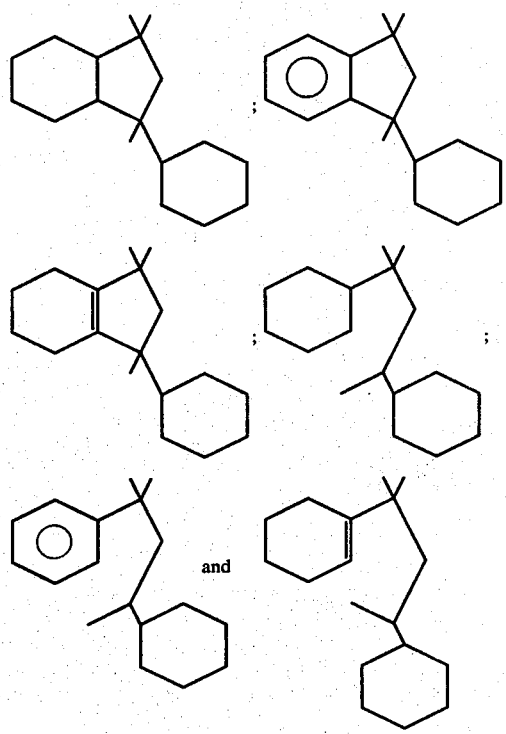

21. The process of claim 18 wherein the reaction product (B) is a dimerization product and the dimerization product is a dimerization product of α-pinene.

22. The process of claim 18 wherein the reaction product (B) is a dimerization product and the dimerization product is a dimerization product of d-limonene.

23. The process of claim 18 wherein the reaction product (B) is a dimerization product and the dimerization product is a dimerization product of turpentine.

* * * * *